(12) United States Patent
Aubin et al.

(10) Patent No.: US 10,919,887 B2
(45) Date of Patent: Feb. 16, 2021

(54) SALTS AND SOLID FORMS OF A MONOBACTAM ANTIBIOTIC

(71) Applicant: Novartis AG, Basel (CH)

(72) Inventors: Eric Aubin, Kembs (FR); Anthony Casarez, San Francisco, CA (US); Andreas Fisch, Basel (CH); Zaixing Li, Shanghai (CN); Mika Lindvall, Oakland, CA (US); Heinz Ernst Moser, San Mateo, CA (US); Michael Mutz, Lörrach (DE); Folkert Reck, Walnut Creek, CA (US); Bernd Ulrich Riebesehl, Loerrach (DE); Marc Schoenhentz, Ungersheim (FR); Vijay Sethuraman, Fremont, CA (US); Robert Lowell Simmons, San Francsico, CA (US)

(73) Assignee: Novartis AG, Basel (CH)

( * ) Notice: Subject to any disclaimer, the term of this patent is extended or adjusted under 35 U.S.C. 154(b) by 228 days.

(21) Appl. No.: 15/762,724

(22) PCT Filed: Sep. 20, 2016

(86) PCT No.: PCT/CN2016/099482
§ 371 (c)(1),
(2) Date: Mar. 23, 2018

(87) PCT Pub. No.: WO2017/050218
PCT Pub. Date: Mar. 30, 2017

(65) Prior Publication Data
US 2018/0273522 A1 Sep. 27, 2018

Related U.S. Application Data

(60) Provisional application No. 62/222,430, filed on Sep. 23, 2015.

(51) Int. Cl.
*C07D 417/14* (2006.01)
*A61P 31/04* (2006.01)

(52) U.S. Cl.
CPC ............ *C07D 417/14* (2013.01); *A61P 31/04* (2018.01); *C07B 2200/13* (2013.01)

(58) Field of Classification Search
CPC .................................................. C07D 417/14
See application file for complete search history.

(56) References Cited

U.S. PATENT DOCUMENTS

| 4,775,670 | A | 11/1988 | Sykes |
| 4,782,147 | A | 11/1988 | Ochiai |
| 5,112,968 | A | 5/1992 | Treuner |
| 9,174,978 | B2 * | 11/2015 | Aulakh ............ C07D 417/14 |
| 9,238,657 | B2 | 1/2016 | Nishitani |
| 10,369,138 | B2 * | 8/2019 | Aulakh ............ A61K 31/427 |
| 2012/0302542 | A1 | 11/2012 | Brown et al. |

FOREIGN PATENT DOCUMENTS

| CL | 19810097302 | | 12/1981 |
| CL | 201401956 | | 11/2014 |
| CL | 201602285 | | 12/2016 |
| CN | 103044416 | | 4/2013 |
| EA | 030850 | B1 | 10/2018 |
| EP | 48953 | A2 | 4/1982 |
| EP | 53816 | A1 | 6/1982 |
| EP | 73061 | A2 | 3/1983 |
| EP | 83039 | A1 | 7/1983 |
| EP | 0093376 | A2 | 11/1983 |
| EP | 93376 | A2 | 11/1983 |
| EP | 95778 | A1 | 12/1983 |
| EP | 96297 | A2 | 12/1983 |
| EP | 177940 | A2 | 10/1985 |
| JP | 61053282 | | 3/1986 |
| JP | 61053283 | | 3/1986 |
| JP | 2013-544276 | A | 12/2013 |
| NL | 8100571 | | 9/1981 |
| WO | 2010/050468 | | 5/2010 |
| WO | 2010/070523 | | 6/2010 |
| WO | 2012/073138 | A1 | 6/2012 |
| WO | 2013/110643 | A1 | 8/2013 |
| WO | WO-2013/110643 | A1 | 8/2013 |
| WO | 2015/103583 | | 7/2015 |
| WO | 2015/148379 | | 10/2015 |
| WO | WO-2015/148379 | A1 | 10/2015 |

OTHER PUBLICATIONS

Extended European Search Report for European Patent Application No. 16848099.4 dated May 27, 2019 (10 pages).
Brown et al., "Pyridone-Conjugated Monobactam Antibiotics with Gram-Negative Activity" J. Med. chem 56:5541-5552, 2013.
Uri, High Degree of Specificity of the Color Reaction for the Aminothiazolyl Oxyimino Beta-Lactam Antibiotics: Aet Chimica Hungarica 128(1):89-91 1991.
Matsuda et al., Preferential Hydrolysis of cis Configuration Compounds at the 3,4 Position of Monobactams by Beta-Lactamase from Morganella Morganii Antimicrobial Agents and Chemotherapy 35(3):458-461, Mar. 1991.
Matsuda et al., "Structure-Activity Relations of 4-Fluoromethyl Monobactams" Journal of Antimicrobial Chemotherapy 19:753-760, 1987.
Neu and Chen, "In vitro Activity and Beta-Lactamase Stability of a new Monobactam, B0-1165" Antimicrobia; Agents Chemotherapy 31(4):505-511, 987.

(Continued)

*Primary Examiner* — Shawquia Jackson
(74) *Attorney, Agent, or Firm* — Clark & Elbing LLP

(57) ABSTRACT

The invention provides new solid forms, salts and polymorphs of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid (referred to herein as Compound X), pharmaceutical compositions containing them, and processes for their manufacture and use in therapy.

9 Claims, 14 Drawing Sheets
Specification includes a Sequence Listing.

(56) References Cited

OTHER PUBLICATIONS

Sendai et al., "Chemical Modification of Sulfazecin Synthesis of 4-(Substituted Methyl)-2-Azetidinone-1-Sulfonic Acid Derivatives" The Journal of Antibiotics 38(3):346-371, Mar. 1985.
Page, "Siderophore Conjugates" Ann NY Acad. Sci. 1277:115-126, 2013.
Tomaras et al., "Adaptation-Based Resistance to Siderophore-Conjugated Antibacterial Agents by Pseudomonas aeruginosa" Antimicrobial Agents and Chemotherapy 57(9):4197-4207, Sep. 2013.
Reck, "Synthesis and Optimization of Novel Monobactams with Activity Against Carbapenem-Resistant Enterobacteriaceae: Identification of LYS228" New Orleans, LA Microbe Jun. 1-2, 2017.
Office Action for Chilean Patent Application No. 201800745 dated Aug. 14, 2019 (13 pages) (English language translation not available).
English language translation of Official Action for Russian Application No. 2018114480/04(022642) dated Jun. 9, 2020 (9 pages).
Berge et al., "Pharmaceutical salts," J Pharm Sci. 66(1):1-19 (1977).
Morissette et al., "High-throughput crystallization: polymorphs, salts, co-crystals and solvates of pharmaceutical solids," Adv Drug Deliv Rev. 56(3):275-300 (2004).
Noriaki Hirayama, "Handbook for preparing crystals of organic compounds—Principle and knowhow," pp. 17-23, 37-40, 45-51, 57-65 (Jul. 25, 2008) (28 pages).
Yusaku Shioji, "Manufacture Technology of Solid Tablet," pp. 9, 12-13 (Jan. 27, 2003) (4 pages).
Noriyuki Takada, "API form screening and selection in drug discovery stage," Pharm Stage 2007, 6(10):20-25 (2007) (8 pages).
Office Action for Japanese Patent Application No. 2018-515607 dated Aug. 25, 2020 (5 pages) (No English language translation provided).
English language translation of Office Action for Japanese Patent Application No. 2018-515607 dated Aug. 25, 2020 (4 pages).

\* cited by examiner

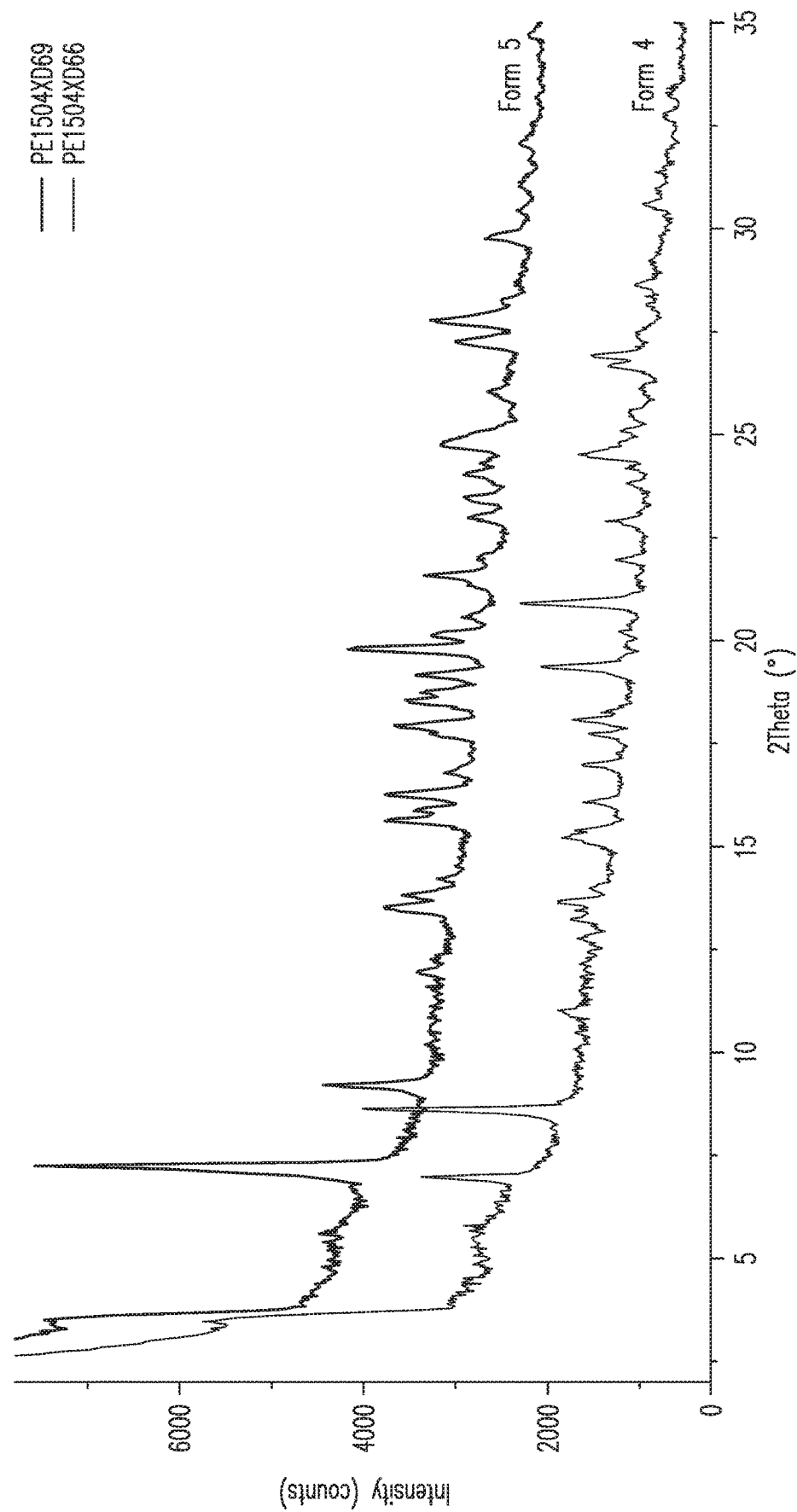

SEQUENCE LISTING

<160> NUMBER OF SEQ ID NOS: 17

<210> SEQ ID NO 1
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 1
tcgcctcgag gcgactgcgc tgacgaattt gg                                  32

<210> SEQ ID NO 2
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 2
aatcgaattc ttactgacca ttaacgccca agc                                 33

<210> SEQ ID NO 3
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 3
tcgcctcgag gcgagcccgc aaccgctgga                                     30

<210> SEQ ID NO 4
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 4
aatcgaattc ttaacgctgc cagtgctcaa tc                                  32

<210> SEQ ID NO 5
<211> LENGTH: 866
<212> TYPE: DNA
<213> ORGANISM: Artificial Sequence
<220> FEATURE:
<223> OTHER INFORMATION: Synthetic Polynucleotide

<400> SEQUENCE: 5
atgggccatc atcatcatca tcacagcagc ggcctggaag ttctgttcca ggggcccgcg    60
agcccgcaac cgctggagca gatcaagcag tctgagagcc agctgagcgg ccgtgtgggt   120
atgatcgaga tggatctggc ttccggccgt acgctgacgg catggcgtgc cgacgaacgt   180
ttcccgatga tgtcgacctt taaagttgtt ctgtgtggtg cggtcttggc acgtgtagac   240
gcgggtgacg aacaactgga gcgcaagatc cattaccgcc aacaggactt ggtcgactac   300
agcccggtta gcgaaaagca cctggcggat ggcatgaccg tgggtgaatt gtgcgccgct   360
gcgattacca tgagcgacaa tagcgcggct aatctgctgt ggcgaccgt tggtggccca    420 gcgggcttga ccgcatttct gcgtcaaatc ggcgataatg ttacgcgtct ggatcgctgg   480
gaaacggagc tgaacgaggc actgccgggt gatgcccgtg ataccacgac tcctgctagc   540
atggcagcga ccctgcgtaa actgctgacc agccagcgtc tgagcgcacg tagccaacgc   600

| | |
|---|---|
| cagctgctgc aatggatggt ggatgaccgc gtggcgggtc cgctgatccg ctccgtcctg | 660 |
| ccagcaggct ggttcattgc ggacaaaact ggtgcctcta agcgtggtgc gcgtggtatc | 720 |
| gtcgcgctgc tgggtccgaa caacaaagcc gaacgtattg tggttatcta tctgcgcgac | 780 |
| accccggcaa gcatggccga gcgcaaccag caaattgcgg gcattggtgc ggcactgatt | 840 |
| gagcactggc agcgttaacg ccggcg | 866 |

<210> SEQ ID NO 6
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 6

| | |
|---|---|
| tcgcctcgag gcgagcccgc aaccgctgga | 30 |

<210> SEQ ID NO 7
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 7

| | |
|---|---|
| aatcgaattc ttaacgctgc cagtgctcaa tc | 32 |

<210> SEQ ID NO 8
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 8

| | |
|---|---|
| gattgagcac tggcagcgtt aagaattcga tt | 32 |

<210> SEQ ID NO 9
<211> LENGTH: 884
<212> TYPE: DNA
<213> ORGANISM: Artificial Sequence
<220> FEATURE:
<223> OTHER INFORMATION: Synthetic Polynucleotide

<400> SEQUENCE: 9

| | |
|---|---|
| atgggccatc atcatcatca tcacagcagc ggcctggaag ttctgttcca ggggcccgcg | 60 |
| actgcgctga cgaatttggt ggccgagccg ttcgcgaaat ggagcaaga ttttggtggt | 120 |
| tcgatcggtg tctacgcgat ggacaccggt agcggtgcca ccgtgagcta ccgtgccgaa | 180 |
| gagcgttttc cgctgtgtag ctctttcaag ggttttctgg ccgcagccgt gctggcacgc | 240 |
| agccaacagc aagcgggcct gctggacacc ccgatccgtt acggcaaaaa tgcgctggtt | 300 |
| ccgtggagcc cgattagcga aaagtacctg accaccggca tgacggtggc ggagttgagc | 360 |
| gctgcggcgg ttcagtattc cgataacgct gcggcaaatc tgctgctgaa agaactgggc | 420 |
| ggtccagcgg gtctgacggc tttcatgcgt tctattggcg acaccacctt cgcttggac | 480 |
| cgctgggagc tggagctgaa cagcgcgatt ccgggcgacg cacgtgatac gagcagcccg | 540 |
| cgtgcagtga ccgagagcct gcagaagctg accctgggca gcgcactggc cgcaccgcag | 600 |
| cgccaacagt tcgtcgattg gctgaagggt aacaccaccg gtaaccatcg tattcgcgca | 660 |

```
gcggtcccgg ctgattgggc agttggtgac aagactggta cgtgcggcgt ttatggtacg      720
gcgaatgact acgcggttgt ttggcctacg ggtcgtgcgc cgatcgtcct ggcggtgtat      780
acccgtgctc cgaacaaaga cgataaacac tccgaagcgg tcatcgccgc agcagcgcgt      840
ctggccctgg aaggcttggg cgttaatggt cagtaacgcc ggcg                      884
```

```
<210> SEQ ID NO 10
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 10
tcgcctcgag gcgactgcgc tgacgaattt gg                                   32

<210> SEQ ID NO 11
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 11
aatcgaattc ttactgacca ttaacgccca agc                                  33

<210> SEQ ID NO 12
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 12
gcttgggcgt taatggtcag taagaattcg att                                  33

<210> SEQ ID NO 13
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 13
ttcactgcag tgaacgttgc gaagcaacgg c                                    31

<210> SEQ ID NO 14
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 14
tcgaggatcc tcgagagcaa aaacaggaag gcaaaatgcc g                         41

<210> SEQ ID NO 15
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 15
ccgtctagac ggatggcctt tttgcgtttc                                      30
```

```
<210> SEQ ID NO 16
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 16
aatcgaattc ttactgacca ttaacgccca agc                          33

<210> SEQ ID NO 17
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 17
aatcgaattc ttaacgctgc cagtgctcaa tc                           32
```

SALTS AND SOLID FORMS OF A MONOBACTAM ANTIBIOTIC

CROSS-REFERENCE TO RELATED APPLICATIONS

This application is a U.S. National Phase filing of International Application Serial No. PCT/CN2016/099482, filed Sep. 20, 2016, and claims the benefit of priority to U.S. Provisional Application No. 62/222,430, filed on Sep. 23, 2015, which is hereby incorporated by reference in its entirety.

FIELD OF THE INVENTION

The present invention relates to salts and crystal forms of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid that are suitable for commercial scale production, as well as pharmaceutical compositions containing these materials, methods of preparing them, and their use in therapy.

BACKGROUND

Over the past several decades, the frequency of antimicrobial resistance and its association with serious infectious diseases have increased at alarming rates. The increasing prevalence of resistance among nosocomial pathogens is particularly disconcerting. Of the over 2 million nosocomial (hospital-acquired) infections occurring each year in the United States, 50 to 60% are caused by antimicrobial-resistant strains of bacteria. The high rate of resistance to commonly used antibacterial agents increases the morbidity, mortality, and costs associated with nosocomial infections. In the United States, nosocomial infections are thought to contribute to or cause more than 77,000 deaths per year and cost approximately $5 to $10 billion annually.

Important causes of Gram-negative resistance include extended-spectrum β-lactamases (ESBLs), serine carbapenemases (KPCs) and metallo-β-lactamases (for example NDM-1) in *Klebsiella pneumoniae, Escherichia coli*, and *Proteus mirabilis*, high-level third-generation cephalosporin (AmpC) β-lactamase resistance among *Enterobacter* species and *Citrobacter freundii*, and multidrug-resistance genes observed in *Pseudomonas, Acinetobacter*, and *Stenotrophomonas*. The problem of antibacterial resistance is compounded by the existence of bacterial strains resistant to multiple antibacterials. For example, *Klebsiella pneumonia* harboring NDM-1 metallo-β-lactamase carries frequently additional serine-β-lactamases on the same plasmid that carries the NDM-1.

Thus there is a need for new antibacterials, particularly antibacterial compounds that are effective against existing drug-resistant microbes, or are less susceptible to development of new bacterial resistance. The current invention provides solid forms of such compounds that are especially well suited for commercial-scale production due to their handling properties under convenient operating conditions for manufacture.

Unpublished patent application number PCT/US2015/022011 describes certain monobactam antibiotics. One compound in that application that shows strong activity against Gram-negative bacteria, including strains that show resistance to other monobactams, is 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid, which is referred to herein as Compound X:

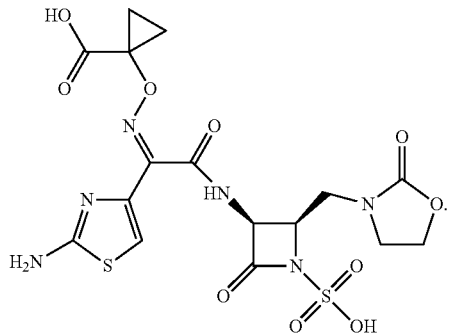

(Compound X)

For manufacturing pharmaceutical compounds and their formulations, it is important that the active compound be in a form that can be conveniently handled and processed in order to obtain a commercially viable, reliable, and reproducible manufacturing process. Compound X and many of its salts are solid at room temperature, and can be produced in various solid forms, depending on the conditions used to produce, purify or crystallize the material. The existence of multiple solid forms, often referred to as polymorphs, is well known for solid pharmaceutical compounds, and the chemical and physical stability as well as handling properties of such compounds often depend on which solid form is used. Accordingly, the selection of a particular solid form of the active drug substance (e.g., a salt form, hydrated or solvated form, or polymorphic form) is often very important in the design of a reliable and reproducible production process, and in storage, handling and distribution of a safe and effective form of the drug substance.

It is generally found that there are advantages in manufacturing a particular solid-state form of a pharmaceutical ingredient, and these are described in "Handbook of Pharmaceutical Salts; Properties, Selection and Use", P. Heinrich Stahl, Camille G. Wermuth (Eds.) (Verlag Helvetica Chimica Acta, Zurich). Methods of manufacturing solid-state forms are also described in "Practical Process Research and Development", Neal G. Anderson (Academic Press, San Diego) and "Polymorphism: In the Pharmaceutical Industry", Rolf Hilfiker (Ed) (Wiley VCH).

The present inventors have discovered certain salts and polymorph forms of Compound X that are particularly suitable for use in the manufacture, storage or administration of Compound X as described herein.

It is important for a drug product to be stable enough to avoid significant degradation when it is shipped and stored under commercially practical conditions. The inventors have discovered that Compound X in solution is preferably used and stored at a pH between 4 and 6, preferably between 4.0 and 5.5, for maximum stability in the presence of moisture. Optimal solution stability is achieved at a pH of about 4.0 to 5.5 Accordingly, the invention provides pharmaceutical compositions comprising Compound X at a pH between 4 and 6, preferably between 4.0 and 5.5, and more preferably at a pH of about 5±0.5 or at pH of 5±0.2. Suitable compositions comprise Compound X in an aqueous solution, such as a dextrose or saline solution, which may be isotonic, and may contain other substances such as stabilizers, antioxidants, buffers or pH modifiers, nutrients, and the like. In some of these embodiments, the desired pH is achieved by combining Compound X and a pH modifier suitable to achieve the desired pH in an aqueous solution. Suitable pH modifiers include but are not limited to sodium hydroxide, sodium carbonate, sodium bicarbonate, potassium carbonate, potassium hydroxide, amines such as TRIS (tris(hydroxymethyl)aminomethane), and amino acids such as arginine, lysine, histidine, and the like. Known monobactams, including aztreonam, have been formulated with arginine.

Suitable pH can be achieved by adding a pH modifier to an aqueous solution of Compound X, or by adding Compound X to an aqueous solution containing the pH modifier. Appropriate quantities of the pH modifier and Compound X can be readily determined by the skilled person. Suitable pH modifiers include sodium hydroxide and arginine. Thus a solution or suspension of Compound X can be treated with sodium hydroxide, or with arginine, to produce a solution comprising a sodium salt or an arginine salt of the Compound. Moreover, this solution can be lyophilized to remove the water and any co-solvents present, leaving a lyophilized solid that comprises Compound X along with the pH modifier, or a salt formed by Compound X and the pH modifier, e.g., the sodium salt or arginine salt of Compound X.

Furthermore, in accordance with the present invention, there are provided a number of solid forms of Compound X that provide handling properties suitable for manufacture on industrial scale, along with methods of producing these polymorphs.

The following enumerated embodiments of the invention are representative:

1. An arginine salt of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid. In some embodiments, the salt is an (L)-arginine salt.
2. A sodium salt of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid.
3. A hydrated solid form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid.
4. The hydrated solid form according to embodiment 3, which consists mainly of a trihydrate of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid.
5. A method to prepare the hydrated solid form according to embodiment 4, which comprises contacting 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid with an atmosphere having relative humidity between 25% and 50% at a temperature between 20° C. and 30° C.
6. A pharmaceutical composition comprising a compound according to any one of embodiments 1-4 and at least one pharmaceutically acceptable carrier or excipient.
7. A crystalline form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid (Form 1) which exhibits at least the following characteristic X-ray powder diffraction peaks (expressed in degrees 2θ): 6.6. 13/4, and 18.8. In some embodiments, Form 1 has additional XRPD peaks as described below.
8. A crystalline form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid (Form 2) which exhibits at least the following characteristic X-ray powder diffraction peaks (expressed in degrees 2θ): 7.5, 19.3, and 20.0. In some embodiments, Form 2 has additional XRPD peaks as described below.
9. A crystalline form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid (Form 3) which exhibits at least the following characteristic X-ray powder diffraction peaks (expressed in degrees 2θ): 7.3, 18.9, and 21.2. In some embodiments, Form 3 has additional XRPD peaks as described below.
10. A crystalline form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid (Form 4) which exhibits at least the following characteristic X-ray powder diffraction peaks (expressed in degrees 2θ): 7.0, 8.6, 19.3 and 20.9. In some embodiments, Form 4 has additional XRPD peaks as described below.
11. A crystalline form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid (Form 5) which exhibits at least the following characteristic X-ray powder diffraction peaks (expressed in degrees 2θ): 7.3, 9.3, and 27.8. In some embodiments, Form 5 has additional XRPD peaks as described below.
12. A crystalline form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid (Form 6) which exhibits at least the following characteristic X-ray powder diffraction peaks (expressed in degrees 2θ): 8.1, 9.2, and 12.8; and optionally by additional peaks at 21.2 and 24.7. In some embodiments, Form 6 has additional XRPD peaks as described below.
13. A crystalline form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid (Form 7) which exhibits at least the following characteristic X-ray powder diffraction peaks (expressed in degrees 2θ): 6.7, 7.3 and 20.3. In some embodiments, Form 7 has additional XRPD peaks as described below.
14. A crystalline form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid (Form 8) which exhibits at least the following characteristic X-ray powder diffraction peaks (expressed in degrees 2θ): 6.2, 21.8 and 25.9. In some embodiments, Form 8 has additional XRPD peaks as described below.
15. A crystalline form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid (Form 9) which exhibits at least the following characteristic X-ray powder diffraction peaks (expressed in degrees 2θ): 6.3, 12.6, and 22.3; and optionally by one or more additional peaks selected from 22.1, 23.1, 27.0 and 27.5. In some embodiments, Form 9 has additional XRPD peaks as described below.

16. A crystalline form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid (Form 10) which exhibits at least the following characteristic X-ray powder diffraction peaks (expressed in degrees 2θ): 6.6, 11.0, and 16.5; and optionally by one or more additional peaks selected from 22.2 and 23.4. In some embodiments, Form 10 has additional XRPD peaks as described below.

17. A crystalline form of 1-(((4-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid (Form 11) which exhibits at least the following characteristic X-ray powder diffraction peaks (expressed in degrees 2θ): 7.4, 9.7, and 29.3; and optionally by one or more additional peaks selected from peaks at 17.0, 19.5, 22.2, 26.3 and 28.1. In some embodiments, Form 11 has additional XRPD peaks as described below.

18. A crystalline form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid (Form 12) which exhibits at least the following characteristic X-ray powder diffraction peaks (expressed in degrees 2θ): 19.0, 20.4, and 24.0; and optionally by one or more additional peaks selected from peaks at 7.3, 24.7, and 27.2. In some embodiments, Form 12 has additional XRPD peaks as described below.

19. A pharmaceutical composition comprising 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid and arginine.

20. The pharmaceutical composition of claim 19, which further comprises a pharmaceutically acceptable carrier.

21. The pharmaceutical composition of claim 20, wherein the carrier is aqueous.

22. The pharmaceutical composition of claim 21, which is at a pH of about 5.0.

23. The pharmaceutical composition of claim 21 or 22, which further comprises at least one excipient selected from sucrose, fructose, trehalose, mannitol, and lactose.

24. A compound according to any one of claims 1-4, or a crystalline form thereof according to any one of claims 7 to 18, for use in therapy.

25. The compound of claim 24, wherein the therapy is the treatment of a Gram-negative bacterial infection.

26. The compound according to claim 24, wherein the bacterium causing the Gram-negative bacterial infection is selected from *Citrobacter, Enterobacter, Eschirichia, Haemophilus, Klebsiella, Morganella, Moraxella, Pseudomonas, Proteus, Salmonella, Serratia, Shigella*, and *Neisseria* bacteria.

27. Use of a compound according to any one of claims 1 to 4, or a crystalline form thereof according to any one of claims 7 to 18, in the manufacture of a medicament for the treatment of a Gram-negative bacterial infection.

28. Use, according to claim 27, wherein the bacterium causing the Gram-negative bacterial infection is a species selected from *Citrobacter, Enterobacter, Eschirichia, Haemophilus, Klebsiella, Morganella, Moraxella, Pseudomonas, Proteus, Salmonella, Serratia, Shigella*, and *Neisseria* bacteria.

29. A method of treatment for a Gram-negative infection, comprising administering to a subject in need thereof a therapeutically effective amount of a compound according to any one of claims 1 to 4, or a crystalline form according to any one of claims 7 to 18, or a pharmaceutical composition according to any one of claims 19-23.

30. The method of claim 29, wherein the bacterium causing the Gram-negative bacterial infection is a species selected from *Citrobacter, Enterobacter, Eschirichia, Haemophilus, Klebsiella, Morganella, Moraxella, Pseudomonas, Proteus, Salmonella, Serratia, Shigella*, or *Neisseria* bacteria.

Thus, in one aspect, the invention provides a crystalline form of Compound X (Form 1) which exhibits at least the following characteristic X-ray powder diffraction peaks (expressed in degrees 2θ): 6.6, 13.4, and 18.8. In one embodiment, Form 1 exhibits at least the following characteristic X-ray powder diffraction peaks: 6.6, 13.4, 16.6, 17.9, 18.8, 20.3, 25.1, and 28.9. In another embodiment, Form 1 exhibits at least the characteristic X-ray powder diffraction peaks shown in List 1, or any subset of at least five peaks selected from List 1. In yet another embodiment, Form 1 exhibits an X-ray powder diffraction pattern substantially the same as that shown in FIG. 1.

In another aspect, the invention provides a crystalline form of Compound X (Form 2) which exhibits at least the following characteristic X-ray powder diffraction peaks (expressed in degrees 2θ): 7.5, 19.3 and 20.0. In one embodiment, Form 2 exhibits at least the following characteristic X-ray powder diffraction peaks: 6.7, 7.5, 13.3, 13.7, 15.3, 17.9, 18.7, 19.3 and 20.0. In another embodiment, Form 2 exhibits at least the characteristic X-ray powder diffraction peaks shown in List 2, or any subset of at least five peaks selected from List 2. In yet another embodiment, Form 2 exhibits an X-ray powder diffraction pattern substantially the same as that shown in FIG. 2.

In another aspect, the invention provides a crystalline form of Compound X (Form 3) which exhibits at least the following characteristic X-ray powder diffraction peaks (expressed in degrees 2θ): 7.3, 18.9, and 21.2; and optionally further including a peak at 8.3. In one embodiment, Form 3 exhibits at least the following characteristic X-ray powder diffraction peaks: 7.3, 13.9, 16.7, 18.9, 20.3, 21.2, and 24.6. In another embodiment, Form 3 exhibits at least the characteristic X-ray powder diffraction peaks shown in List 3, or any subset of at least five peaks selected from List 3. In yet another embodiment, Form C exhibits an X-ray powder diffraction pattern substantially the same as that shown in FIG. 4.

In another aspect, the invention provides a crystalline form of Compound X (Form 4) which exhibits at least the following characteristic X-ray powder diffraction peaks (expressed in degrees 2θ): 7.0, 8.6, 19.3 and 20.9. In one embodiment, Form 4 exhibits at least the following characteristic X-ray powder diffraction peaks: 7.0, 8.6, 15.2, 17.0, 18.0, 19.3, 20.9, 24.5, and 26.9. In another embodiment, Form 4 exhibits at least the characteristic X-ray powder diffraction peaks shown in List 4, or any subset of at least five peaks selected from List 4. In yet another embodiment, Form 4 exhibits an X-ray powder diffraction pattern substantially the same as that shown in FIG. 5.

In another aspect, the invention provides a crystalline form of Compound X (Form 5) which exhibits at least the following characteristic X-ray powder diffraction peaks (expressed in degrees 2θ): 7.3, 9.3, and 27.8; and optionally further including a peak at 19.9. In one embodiment, Form 5 exhibits at least the following characteristic X-ray powder diffraction peaks: 7.3, 9.3, 16.3, 18.6, 19.2, 19.9, 21.7, 24.1, 24.9, 27.3, 27.8 and 29.8. In another embodiment, Form 5 exhibits at least the following characteristic X-ray powder diffraction peaks shown in List 5, or any subset of at least five peaks selected from List 5. In yet another embodiment, Form 5 exhibits an X-ray powder diffraction pattern substantially the same as that shown in FIG. 6.

In another aspect, the invention provides a crystalline form of Compound X (Form 6) which exhibits at least the following characteristic X-ray powder diffraction peaks (expressed in degrees 2θ): 8.1, 9.2, 12.8, 21.2, and 24.7. In one embodiment, Form 6 exhibits at least the following characteristic X-ray powder diffraction peaks: 8.1, 9.2, 12.8, 13.9, 14.4, 16.7, 20.1, 21.2, 24.7, and 26.6. In another embodiment, Form 6 exhibits at least the characteristic X-ray powder diffraction peaks shown in List 6, or any subset of at least five peaks selected from List 6. In yet another embodiment, Form 6 exhibits an X-ray powder diffraction pattern substantially the same as that shown in FIG. 7.

In another aspect, the invention provides a crystalline form of Compound X (Form 7) which exhibits at least the following characteristic X-ray powder diffraction peaks (expressed in degrees 2θ): 6.7, 7.3 and 20.3. In one embodiment, Form 7 exhibits at least the following characteristic X-ray powder diffraction peaks: 6.7, 7.3, 17.6, 18.0, 20.3, and 24.9. In another embodiment, Form 7 exhibits at least the characteristic X-ray powder diffraction peaks shown in List 7, or any subset of at least five peaks selected from List 7. In yet another embodiment, Form 7 exhibits an X-ray powder diffraction pattern substantially the same as that shown in FIG. 8.

In another aspect, the invention provides a crystalline form of Compound X (Form 8) which exhibits at least the following characteristic X-ray powder diffraction peaks (expressed in degrees 2θ): 6.2, 21.8, and 25.9. In one embodiment, Form 8 exhibits at least the following characteristic X-ray powder diffraction peaks: 6.2, 17.8, 20.7, 21.8, and 25.9. In another embodiment, Form 8 exhibits at least the characteristic X-ray powder diffraction peaks shown in List 8, or any subset of at least five peaks selected from List 8. In yet another embodiment, Form 8 exhibits an X-ray powder diffraction pattern substantially the same as that shown in FIG. 9.

In one aspect of the invention, the polymorphs of the invention have crystalline properties and are preferably at least 50% crystalline, more preferably at least 60% crystalline, still more preferably at least 70% crystalline and most preferably at least 80% crystalline. Crystallinity can be estimated by conventional X-ray diffractometry techniques or by infra-red spectroscopic techniques.

In some embodiments, the solid form of Compound X comprises one or more of the Forms described herein. A solid form of Compound X can include two or more of these Forms, i.e., it can be a mixture of two or more Forms. In some embodiments, a sample of the solid form mainly consists of a single Form selected from Forms 1-8, meaning that 50% or more of the material is of one solid Form. Relative amounts of various Forms in a mixture can be determined from XRPD data. As described herein, some of the Forms can evolve or interconvert under suitable conditions, such as Forms 4 and 5, which can occur as a mixture, and can interconvert depending on the relative humidity and temperature at which the material is maintained.

In one aspect of the invention, the polymorphs of the invention are from 50%, 60%, 70%, 80% or 90% to 95%, 96%, 97%, 98%, 99% or 100% crystalline.

In the present specification, X-ray powder diffraction peaks (expressed in degrees 2θ) are measured using copper X-rays with a wavelength of 1.5406 Å (alpha1) and 1.5444 Å (alpha2). Peak locations are reported in degrees 2θ and are understood to be subject to small numerical variations and it should thus be understood that the angles are subject to variation of ±0.2°.

The crystalline forms of the present invention can exist in either unsolvated or solvated forms. The term 'solvate' is used herein to describe a molecular complex comprising the compound of the invention and an amount of one or more pharmaceutically acceptable solvents. Examples of pharmaceutically acceptable solvents include ethanol and water. The term 'hydrate' is employed when the solvent is water. Several polymorphs of Compound X as described herein are hydrates.

In one aspect, the invention provides a salt or crystalline form defined herein for use in therapy. In another aspect, the invention provides a method of treatment by therapy, comprising administering to a subject in need thereof a pharmaceutically acceptable amount of a salt or crystalline form according to the invention.

In one aspect, the invention provides the use of a salt or crystalline form defined herein in the manufacture of a medicament for use in therapy.

In one embodiment, the therapy is the treatment of an infection caused by a Gram-negative bacterium.

The invention also provides processes for the preparation of the crystalline forms described herein. Thus, in one aspect, the invention provides a process for the preparation of any of Forms 1, 2, 3, 4, 5, 6, 7, and 8 as described herein comprising the crystallisation of the desired Form from a solution of Compound X, using solvent systems and conditions described in the Examples provided herein.

In the context of the present invention, references herein to "treatment" include references to curative, palliative and prophylactic treatment, unless there are specific indications to the contrary. The terms "therapy, "therapeutic" and "therapeutically" should be construed in the same way.

Compound X is typically administered by injection or infusion, and may be prepared for administration by dissolving Compound X in a suitable amount of water or of an aqueous solution such as dextrose or saline, e.g., isotonic dextrose or saline.

Optionally, the formulated composition may also include a pH modifier such as sodium hydroxide, sodium bicarbonate, sodium carbonate, potassium hydroxide, potassium carbonate, calcium hydroxide, magnesium hydroxide, meglumine, TRIS, or an amino acid (e.g., lysine, histidine, or arginine) in quantity sufficient to provide a desired pH, such as a pH between 4 and 6. While the amino acids used in the examples were (L)-amino acids, a (D)-amino acid or racemic mixture could be used instead. Pharmaceutical compositions comprising Compound X in solution are typically adjusted to a pH between 4.5 and 5.5, often or at a pH of about 5, such as between pH 4.8 and 5.2.

In some embodiments, Compound X is formulated with a pH modifier in aqueous solution, and is then lyophilized to a solid form for storage and distribution. For administration, one can reconstitute the lyophilized drug product by adding an aqueous carrier, typically a sterile aqueous carrier such as water or an isotonic dextrose or saline solution, or other IV solution such as Ringer's, Lactated Ringer's, or Hartmann's solution. Accordingly, the invention also provides a lyophilizate (a solid prepared by lyophilization) comprising Compound X and a pH modifier such as those mentioned above, e.g. (L)-arginine, (L)-lysine, meglumine, TRIS, of sodium hydroxide. Optionally, other excipients such as sucrose may be included. In one embodiment, a solution of Compound X and arginine (two equivalents) is prepared, and the pH is adjusted to a pH between 4.8 and 5.2 using, for example, sodium hydroxide or hydrochloric acid as needed. The solution is then lyophilized to a white or slightly yellow solid, which is stable for storage and can readily be reconstituted with a suitable sterile aqueous solution for intravenous administration.

In another embodiment, a solution of Compound X, sucrose, and arginine (two equivalents) in water suitable for injection is prepared, and the pH is adjusted to a pH between 4.8 and 5.2 using, for example, sodium hydroxide or hydrochloric acid as needed. The solution is then lyophilized to a white or slightly yellow solid, which is stable for storage and can readily be reconstituted with a suitable sterile aqueous solution for intravenous administration.

The salts and crystalline forms of the present invention may be administered alone or in combination with one or more other drugs. Generally, they will be administered as a formulation in association with one or more pharmaceutically acceptable excipients. The term "excipient" is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form. Pharmaceutical compositions may also comprise a carrier, which is a substantially inert material, often a liquid, used to dilute the active ingredient(s). Suitable carriers are known in the art, and include sterile water and sterile solutions of saline or dextrose, for example.

Pharmaceutical compositions suitable for the delivery of the solid forms of Compound X and methods for their preparation will be readily apparent to those skilled in the art. Such compositions and methods for their preparation may be found, for example, in REMINGTON'S PHARMACEUTICAL SCIENCES, 19th Edition (Mack Publishing Company, 1995).

For administration to human patients, the total daily dose of the salt or crystalline form is typically in the range 1000 mg to 10,000 mg, or between 2000 mg and 8000 mg, or between 3000 mg and 8000 mg, or between 4000 mg and 6000 mg, depending on the condition of the subject and parameters such as the subject's body weight, age, and gender. The total daily dose may be administered in a single dose, or it may be divided into two or more doses and may, at the physician's discretion, fall outside of the typical range given herein. Typically, the daily dosage would be delivered via intravenous injection or by infusion, and would be administered in one, two, three or four doses, that cumulatively provide the desired total daily dosage. Infusion may be rapid, or it may be performed over a period of between about 15 minutes and 4 hours, commonly over a period of 1-3 hours. A typical dosing schedule would provide three or four infusions daily, each lasting 0.25-2 hours or 0.25-3 hours, delivering 1 to 2 or 1 to 2.5 grams of Compound X per dose, and a typical total daily dose would be 3-8 grams. For example, a dosing schedule may deliver 2 grams of Compound X per infusion, with three one-hour infusions per day. Alternatively, a single infusion of 2-6 grams, or 3-5 grams over 1 or 1.5 or 2 or 2.5 or 3 hours may be used. The above dosages are based on an average human subject having a weight of about 60 kg to 70 kg, and may be scaled suitably for other subjects. The physician will readily be able to determine doses for subjects whose weight falls outside this range, such as infants and the elderly.

BRIEF DESCRIPTION OF THE FIGURES

The invention will now be illustrated by the following non-limiting examples. In the examples the following figures are presented:

FIG. 6A: X-ray powder diffraction pattern of Form 5 overlaid on XPRD for FIG. 4.

GENERAL EXPERIMENTAL DETAILS

Figure 1:
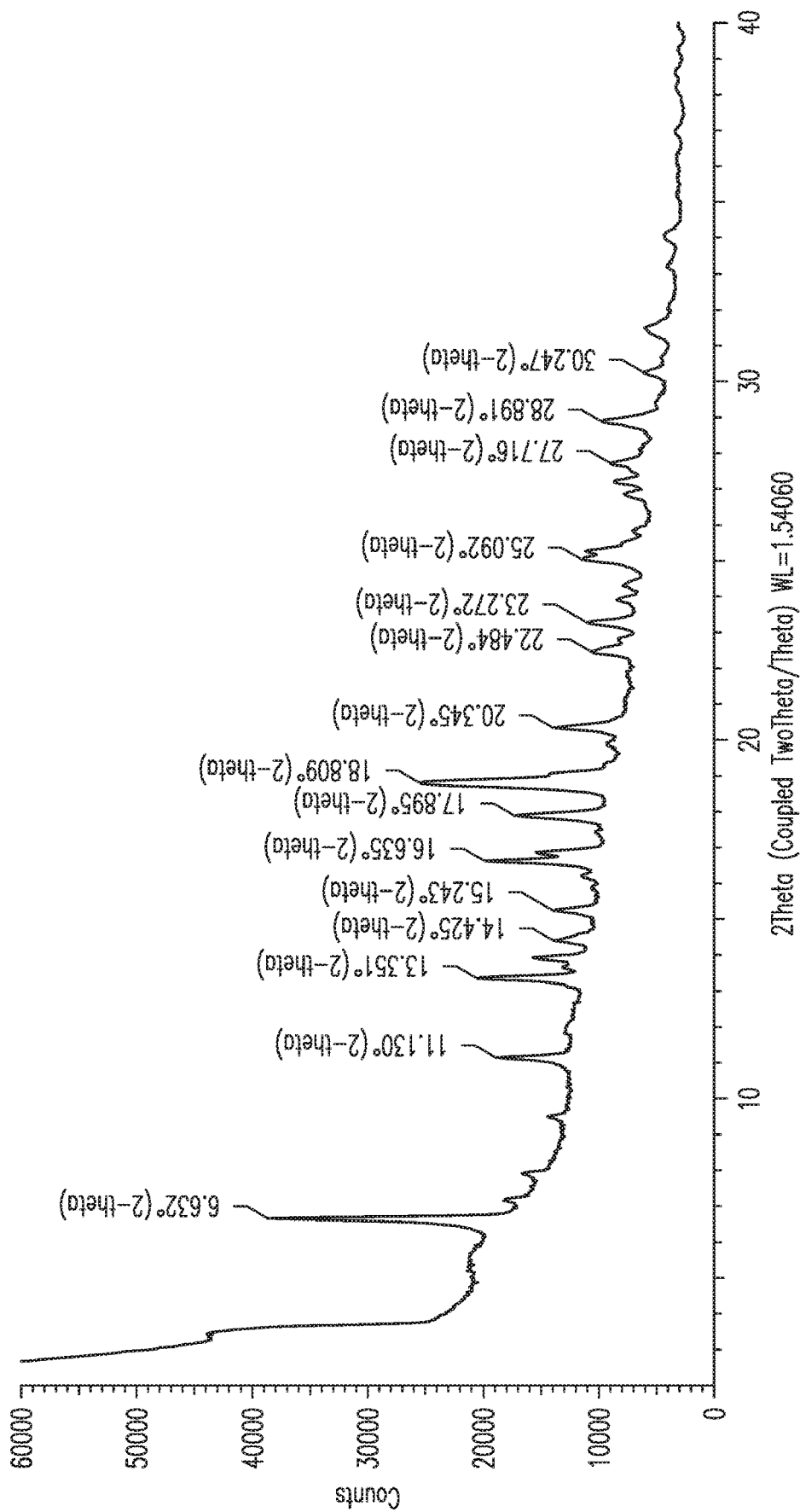
FIG. 1: X-ray powder diffraction pattern of Form 1.

Each sample (few milligrams) is placed between three polymer foils (Kapton® and/or polypropylene). It is worth noting that Kapton® exhibits a broad peak with a weak intensity around $2\theta=5.5°$.

The sample is then placed in a PANALYTICAL X'PERT PRO MPD diffractometer configured in transmission mode, and analyzed using conditions indicated below. The analyses are performed between 2° and 50° (unless stated otherwise).
Radiation: $CuK_\alpha$
Generator settings: 40 kV and 40 mA
Step size: 0.026°
Steps: 1828
Measurement type: Repeated scan (3/5/20 times)

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, METHODS OF ORGANIC SYNTHESIS, Thieme, Volume 21).
General Conditions Mass spectra were acquired on LC-MS, SFC-MS, or GC-MS systems using electrospray, chemical and electron impact ionization methods from a range of instruments of the following configurations: Waters ACQUITY UPLC system and equipped with a ZQ 2000 or SQD MS system where (M+1) refers to the protonated molecular ion of the chemical species, (M+) refers to the unprotonated quaternary ammonium cation, (M+Na) refers to the sodium-incorporated ion and (M−1) refers to the deprotonated molecular ion of the chemical species.

NMR spectra were run on Bruker AVANCE 500 MHz or Varian 400 MHz NMR spectrometers using ICON-NMR, under TopSpin program control. Spectra were measured at 298K, unless indicated otherwise, and were referenced relative to the solvent resonance.
Instrumentation
MS Methods:

Using Agilent 1100 HPLC systems with an Agilent 6110 Mass Spectrometer
Method 2m_acidic:

| | |
|---|---|
| Column | Kinetex C18 50 × 2.1 mm, 2.6 µm |
| Column | 50° C. |

-continued

| | |
|---|---|
| Temperature | |
| Eluents | A: H₂O, B: acetonitrile, both containing 0.1% TFA |
| Flow Rate | 1.2 mL/min |
| Gradient | 2% to 88% B in 1.30 min, 0.15 min 95% B |

Method 2m_acidic_polar:

| | |
|---|---|
| Column | Kinetex C18 50 × 2.1 mm, 2.6 μm |
| Column Temperature | 50° C. |
| Eluents | A: H₂O, B: acetonitrile, both containing 0.1% TFA |
| Flow Rate | 1.2 mL/min |
| Gradient | 1% to 30% B in 1.30 min, 0.15 min 98% B |

Preparation of Compound X

Intermediate A: ((2S,3S)-3-(((benzyloxy)carbonyl)amino)-1-(2,4-dimethoxybenzyl)-4-oxoazetidin-2-yl)methyl methanesulfonate

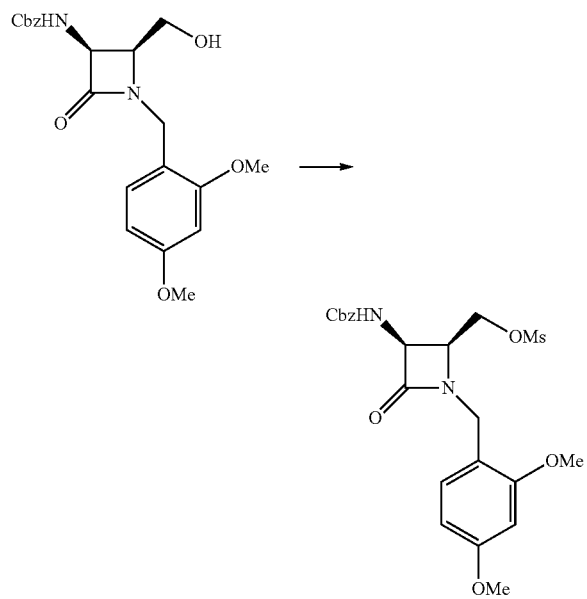

To a solution of benzyl ((2S,3S)-1-(2,4-dimethoxybenzyl)-2-(hydroxymethyl)-4-oxoazetidin-3-yl)carbamate (5.37 g, 13.41 mmol) and TEA (3.72 mL, 26.8 mmol) in DCM at 0° C. was added methanesulfonyl chloride (MsCl) (1.15 mL, 14.75 mmol). After stirring at 0° C. for 1 h, it was diluted with water/DCM and the layers were separated. The aqueous layer was extracted with DCM (2×) and the combined organic layers were washed with brine, dried over Na₂SO₄ and concentrated in vacuo. The crude residue was taken up in toluene and concentrated (2×), affording the title compound as an off white solid. It was used as such in subsequent reactions. LCMS: R$_t$=0.86 min, m/z=479.2 (M+1) Method 2m_acidic.

The starting material for this step can be made using the following approaches or some combination of steps based on these approaches. In a first approach, a protected chiral aldehyde is condensed with 2,4-dimethoxybenzylamine to make a chiral imine.

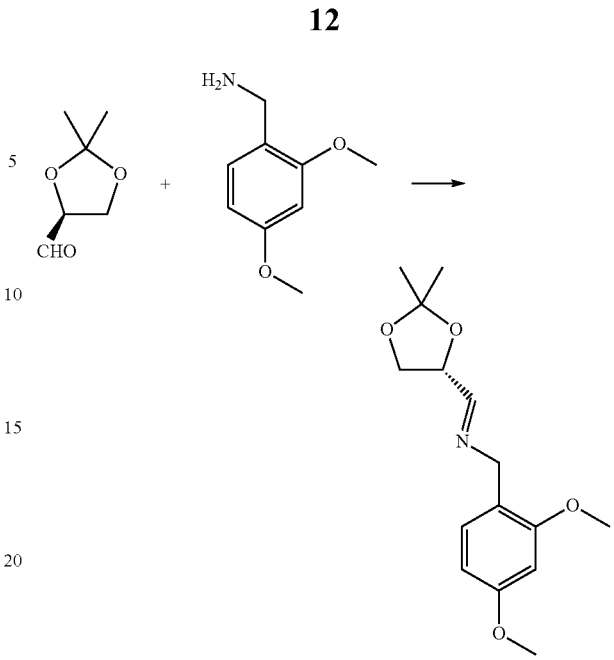

The chiral aldehyde is known, and can be made from citric acid:

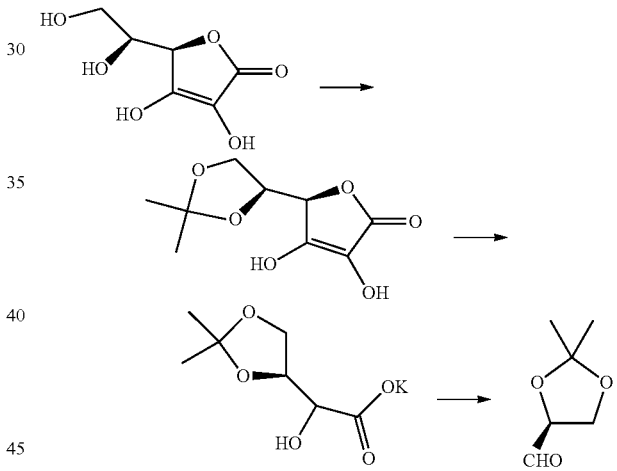

The chiral imine can be reacted with protected forms of glycine such as these:

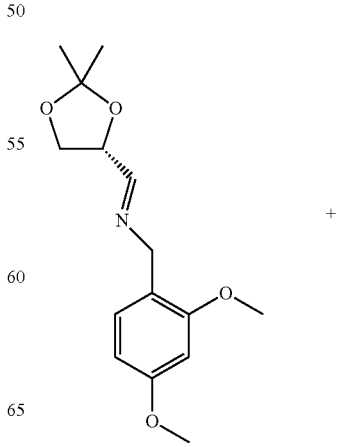

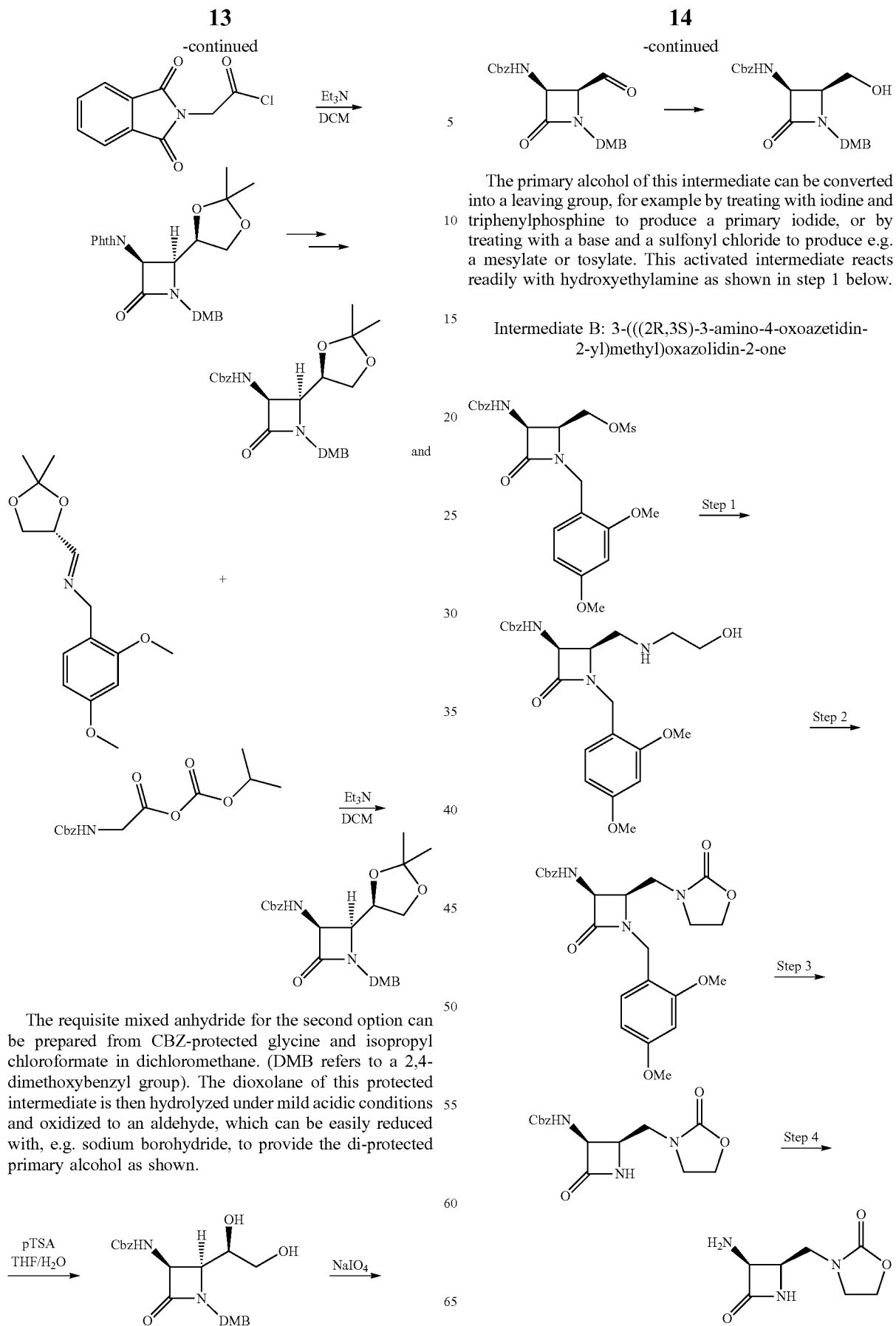

The primary alcohol of this intermediate can be converted into a leaving group, for example by treating with iodine and triphenylphosphine to produce a primary iodide, or by treating with a base and a sulfonyl chloride to produce e.g. a mesylate or tosylate. This activated intermediate reacts readily with hydroxyethylamine as shown in step 1 below.

Intermediate B: 3-(((2R,3S)-3-amino-4-oxoazetidin-2-yl)methyl)oxazolidin-2-one

The requisite mixed anhydride for the second option can be prepared from CBZ-protected glycine and isopropyl chloroformate in dichloromethane. (DMB refers to a 2,4-dimethoxybenzyl group). The dioxolane of this protected intermediate is then hydrolyzed under mild acidic conditions and oxidized to an aldehyde, which can be easily reduced with, e.g. sodium borohydride, to provide the di-protected primary alcohol as shown.

Step 1: Benzyl ((2R,3S)-1-(2,4-dimethoxybenzyl)-2-(((2-hydroxyethyl)amino)methyl)-4-oxoazetidin-3-yl)carbamate To a solution of ((2S,3S)-3-(((benzyloxy)carbonyl)amino)-1-(2,4-dimethoxybenzyl)-4-oxoazetidin-2-yl)methyl methanesulfonate (6.43 g, 13.4 mmol) in Acetonitrile (44.8 ml) was added ethanolamine (8.13 ml, 134 mmol) followed by DIEA (7.0 ml, 40 mmol). The solution was heated to 80° C. for 20 h, whereupon it was cooled to rt, diluted with EtOAc, washed with water, dried over $Na_2SO_4$ and concentrated in vacuo, to afford the title compound (4.47 g, 75%) as a white solid. LCMS: $R_t$=0.60 min, m/z=444.2 (M+1).

Step 2: Benzyl ((3S,4R)-1-(2,4-dimethoxybenzyl)-2-oxo-4-((2-oxooxazolidin-3-yl)methyl)azetidin-3-yl)carbamate To a solution of benzyl ((2R,3S)-1-(2,4-dimethoxybenzyl)-2-(((2-hydroxyethyl)amino)methyl)-4-oxoazetidin-3-yl)carbamate (4.47 g, 10.08 mmol) in chloroform (50 ml) was added carbonyldiimidazole (CDI) (4.90 g, 30.2 mmol). After stirring at rt for 30 min, the reaction mixture was concentrated in vacuo. The crude residue was purified via silica gel chromatography (MeOH-DCM, 0-5%), affording the title compound (3.84 g, 81%) as a white foam. LCMS: $R_t$=0.76 min, m/z=470.1 (M+1).

Step 3: Benzyl ((3S,4R)-2-oxo-4-((2-oxooxazolidin-3-yl)methyl)azetidin-3-yl)carbamate Prepared analogously to a preparation in Mastalerz et al. *J. Med. Chem.* 1988, 31, 1190, using benzyl ((3S,4R)-1-(2,4-dimethoxybenzyl)-2-oxo-4-((2-oxooxazolidin-3-yl)methyl)azetidin-3-yl)carbamate (3.84 g, 8.18 mmol), $K_2S_2O_8$ (3.10 g, 11.5 mmol) and $K_2HPO_4$ (1.852 g, 10.6 mmol) in ACN:water (2:1, 136 mL) and heating for 40 min at 90° C. More $K_2S_2O_8$ (663 g, 2.45 mmol) and $K_2HPO_4$ (370 mg, 2.13 mmol) were added and the mixture was heated for another 3 h. More $K_2S_2O_8$ (332 mg, 1.23 mmol) and $K_2HPO_4$ (185 mg, 1.06 mmol) were added, and it was heated for an additional 2 h, whereupon it was concentrated in vacuo, removing most of the ACN. The mixture was diluted with brine/EtOAc and the layers were separated. The aqueous layer was extracted with EtOAc (3x) and the combined organic layers were dried over $Na_2SO_4$. The crude residue was purified via silica gel chromatography (EtOAc-Heptane, 0-100% then MeOH-DCM, 10%) to afford the title compound (1.61 g, 62%) as a beige foam. LCMS: $R_t$=0.51 min, m/z=320.0 (M+1) Method 2m_acidic.

Step 4: 3-(((2R,3S)-3-amino-4-oxoazetidin-2-yl)methyl)oxazolidin-2-one

Prepared according to Malmström et al. *Bioorg. Med. Chem. Lett.* 2012, 22, 5293, using benzyl ((3S,4R)-2-oxo-4-((2-oxooxazolidin-3-yl)methyl)azetidin-3-yl)carbamate (96 mg, 0.30 mmol) and Pd/C 10% Degussa type 101 (10%, 64 mg) and hydrogen in EtOH:MeOH (4:1, 1.5 mL) for 1 h. The crude residue was used as such in the following step. LCMS: $R_t$=0.11 min, m/z=186.0 (M+1) Method 2m_acidic.

Compound X: 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid

Step 1: Benzhydryl 1-(((Z)-(1-(2-((tert-butoxycarbonyl)amino)thiazol-4-yl)-2-oxo-2-(((3S,4R)-2-oxo-4-((2-oxooxazolidin-3-yl)methyl)azetidin-3-yl)amino)ethylidene)amino)oxy)cyclopropanecarboxylate To a solution of (Z)-2-((1-((benzhydryloxy)carbonyl)cyclopropoxy)imino)-2-(2-((tert-butoxycarbonyl)amino)thiazol-4-yl)acetic acid (854 mg, 1.59 mmol) prepared according to published patent application US2011/0190254, Intermediate B (324 mg, 1.75 mmol) and HATU (785 mg, 2.07 mmol) in DMF (7.9 mL), DIPEA was added (832 µL, 4.77 mmol). After 1 h of stirring, it was poured into water and extracted with EtOAc. Brine was added to the aqueous layer, and it was further extracted with ethyl acetate (EtOAc) (3x). The combined organic layers were dried over $Na_2SO_4$ and concentrated in vacuo. The crude residue was purified via silica gel chromatography (0-10% MeOH-DCM) to afford the title compound (1.09 g, 97%) as a beige foam. LCMS: $R_t$=0.97 min, m/z=705.3 (M+1) Method 2m_acidic.

Instead of HATU, a variety of other coupling reagents can be used, such as any of the typical carbodiimides, or CDMT (2-chloro-4,6-dimethoxy-1,3,5-triazine) and N-methylmorpholine to form the amide bond generated in Step 1.

Step 2: (3S,4R)-3-((Z)-2-((1-((benzhydryloxy)carbonyl)cyclopropoxy)imino)-2-(2-((tert-butoxycarbonyl)amino)thiazol-4-yl)acetamido)-2-oxo-4-((2-oxooxazolidin-3-yl)methyl)azetidine-1-sulfonic acid Benzhydryl 1-(((Z)-(1-(2-((tert-butoxycarbonyl)amino)thiazol-4-yl)-2-oxo-2-(((3S,4R)-2-oxo-4-((2-oxooxazolidin-3-yl)methyl)azetidin-3-yl)amino)ethylidene)amino)oxy)cyclopropanecarboxylate (1.00 g, 1.42 mmol) in DMF (7.0 mL) at 0° C. was treated with $SO_3$.DMF (448 mg, 2.84 mmol). After 2 h of stirring at rt, the solution was poured into ice-cold brine and extracted with EtOAc (3x). The combined organic layers were dried over $Na_2SO_4$ and concentrated in vacuo, affording the title compound (assumed quantitative) as a white solid. LCMS: Rt=0.90 min, m/z=785.2 (M+1) Method 2m_acidic.

Step 3: 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid

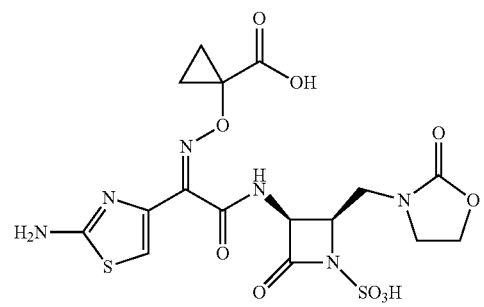 [SMILES: Nc1nc(/C(=N/OC2(C(=O)O)CC2)C(=O)N[C@@H]2C(=O)N(S(=O)(=O)O)[C@@H]2CN2CCOC2=O)cs1]

To a solution of (3S,4R)-3-((Z)-2-((1-((benzhydryloxy)carbonyl)cyclopropoxy)imino)-2-(2-((tert-butoxycarbonyl)amino)thiazol-4-yl)acetamido)-2-oxo-4-((2-oxooxazolidin-3-yl)methyl)azetidine-1-sulfonic acid (1.10 g, 1.40 mmol) in DCM (1.5 mL) at 0° C., TFA (5.39 mL, 70.0 mmol) was added, and after 10 minutes, the ice bath was removed. Additional TFA (3.24 mL, 42.0 mmol) was added after 1 hr at rt and the solution was diluted with DCM and concentrated in vacuo after an additional 30 min. Optionally, anisole may be added to the TFA reaction to help reduce by-product formation, which may increase the yield of desired product in this step. The crude residue was purified by reverse phase prep HPLC (XSelect CSH, 30×100 mm, 5 μm, C18 column; ACN-water with 0.1% formic acid modifier, 60 mL/min), affording the title compound (178 mg, 23%) as a white powder. LCMS: $R_t$=0.30 min, m/z=518.9 (M+1) Method 2m_acidic; $^1$H NMR (400 MHz, DMSO-$d_6$) δ 9.27 (d, J=9.0 Hz, 1H) 6.92 (s, 1H) 5.23 (dd, J=9.1, 5.7 Hz, 1H) 4.12-4.23 (m, 3H) 3.72-3.62 (m, 2H assumed; obscured by water) 3.61-3.52 (m, 1H assumed; obscured by water) 3.26 (dd, J=14.5, 5.9 Hz, 1H) 1.36 (s, 4H). $^1$H NMR (400 MHz, $D_2O$) δ 7.23 (s, 1H), 5.48 (d, J=5.8 Hz, 1H), 4.71-4.65 (m, 1H), 4.44 (t, J=8.2 Hz, 2H), 3.89-3.73 (m, 3H), 3.54 (dd, J=14.9, 4.9 Hz, 1H), 1.65-1.56 (m, 2H), 1.56-1.46 (m, 2H). The product of this process is amorphous. Compound X can be crystallized from acetone, ethanol, citrate buffer at pH 3 (50 mM), or acetate buffer at pH 4.5 (50 mM), in addition to solvents discussed below.

Instrumentation

DSC: Pyris Diamond DSC, Nitrogen gas (20 mL/min)
TGA: Pyris 1 TGA, Nitrogen gas (20 mL/min), scanning at 10° C./min
XRPD: X'Pert Pro MPD Panalytical, Cu anode, 40 kV at 40 mA current
  Tube anode: (Cu)
  Generator tension: 40 kV
  Tube current: 40 mA
  Start angle [2 θ]: 3
  End angle [2 θ]: 40
  Scan time 2 minutes Form 1 and Form 2

Figure 2:
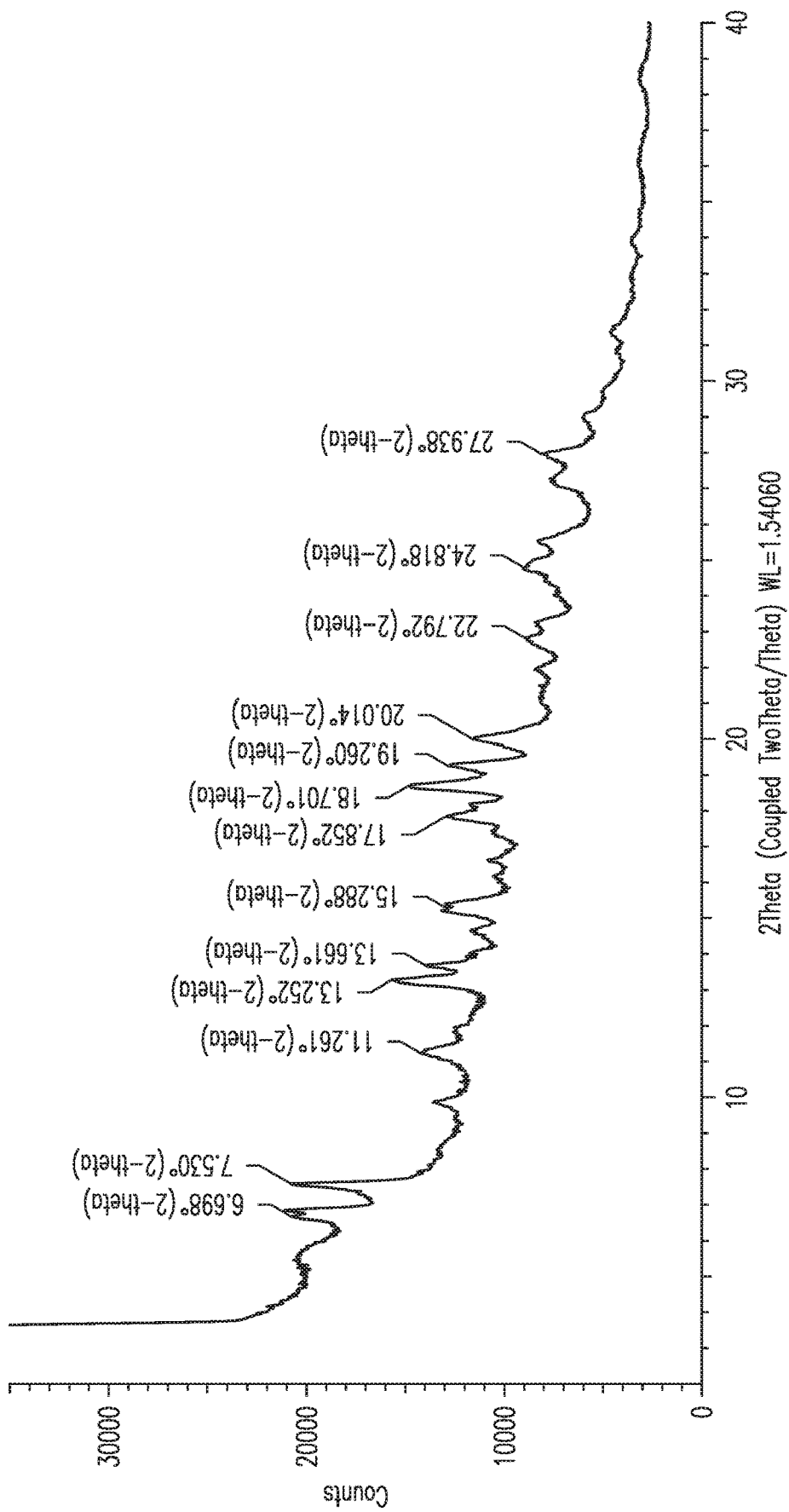
FIG. 2: X-ray powder diffraction pattern of Form 2.

Compound X was prepared as described above and crystallized from solvent to provide materials having the X-ray powder diffraction pattern (XRPD) in FIG. 1 or FIG. 2. These represent two separate batches of crystalline material, and are referred to herein as Form 1 and Form 2. Forms 1 and 2 have some similar XRPD peaks, and the XRPD for Form 2 shows broadened lines, so the product identified as Form 2 may contain some Form 1 material, or both samples may be mixtures of crystal forms. These two Forms were substantially anhydrous, containing less than about 1% water by weight according to Karl Fischer analysis.

Figure 3:
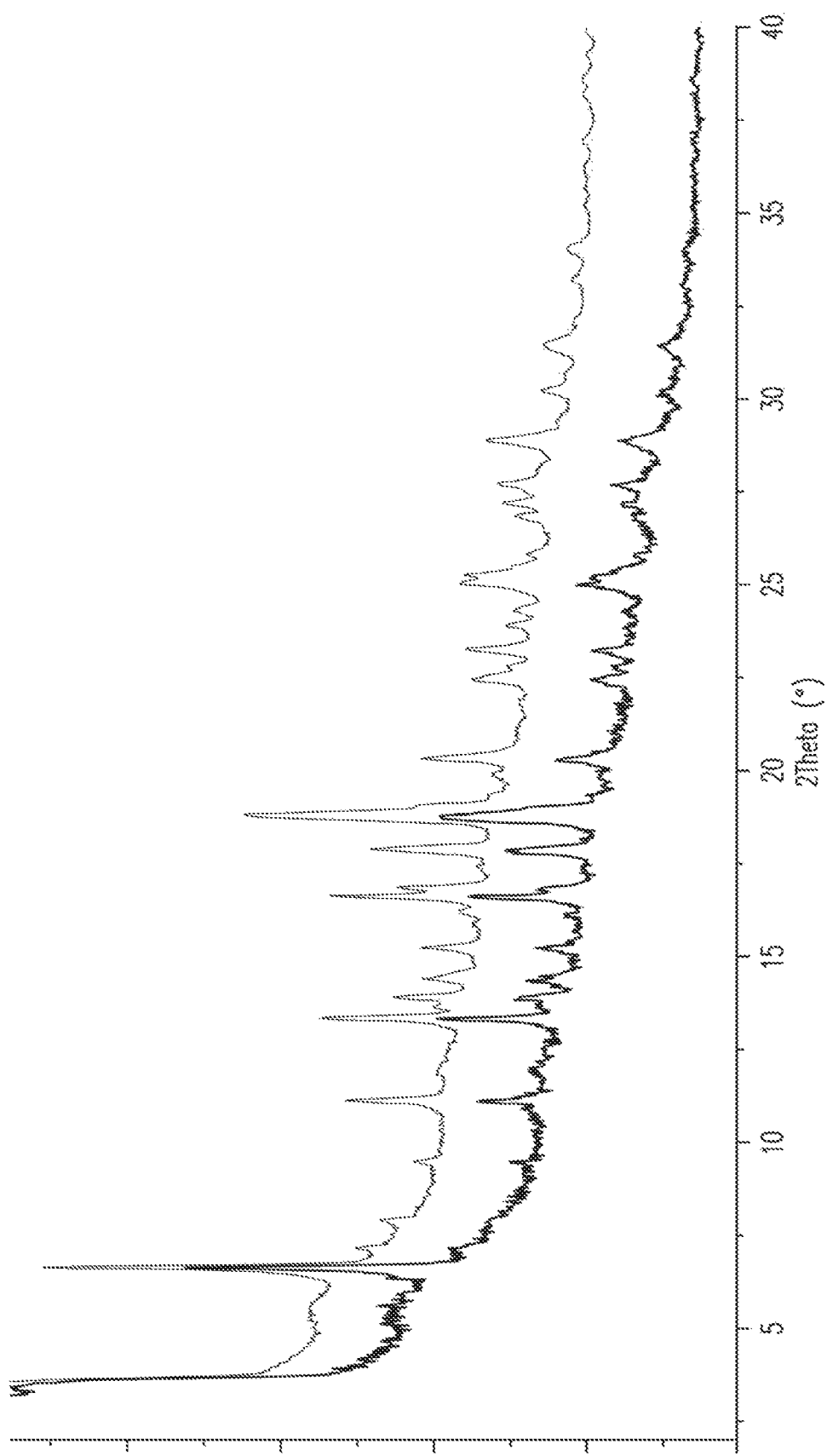
FIG. 3: X-ray powder diffraction pattern of Form 1 after stirring with acetone, overlaid by the XRPD for Form 1 for comparison.

Compound X of Form 1 (1.2 g) was suspended in 12 mL acetone and stirred for 3 days at 20° C. The sample does not appear to evolve: while some line broadening occurred, the XRPD of the product (FIG. 3) still appears generally consistent with Form 1.

The sample giving the XRPD in FIG. 1 exhibited a strong exotherm during DSC at about 205° C., and gradual loss of mass via TGA amounting to about 2% loss by 180° C.

The sample that produced the XRPD in FIG. 2 (Form 2) exhibited a strong exotherm during DSC at about 203° C., and slightly greater loss of mass (3.7%) by 160° C. compared to Form 1.

| List 1: XRPD peak listing for Form 1 (2Theta: most intense peaks are underlined) ||
| --- | --- |
| 1 | <u>6.6</u> |
| 2 | 11.1 |
| 3 | <u>13.4</u> |
| 4 | 14.4 |
| 5 | 15.2 |
| 6 | <u>16.6</u> |
| 7 | <u>17.9</u> |
| 8 | <u>18.8</u> |
| 9 | <u>20.3</u> |
| 10 | 22.5 |
| 11 | 23.3 |
| 12 | <u>25.1</u> |
| 13 | 27.7 |
| 14 | <u>28.9</u> |
| 15 | 30.2 |

Form 1 can also be characterized by a subset of these peaks, for example the peaks at 6.6, 13.4 and 18.8.

| List 2: XRPD peak listing for Form 2 (2Theta: most intense peaks are underlined) ||
| --- | --- |
| 1 | <u>6.7</u> |
| 2 | <u>7.5</u> |
| 3 | 11.3 |
| 4 | <u>13.3</u> |
| 5 | <u>13.7</u> |
| 6 | <u>15.3</u> |
| 7 | <u>17.9</u> |
| 8 | <u>18.7</u> |
| 9 | <u>19.3</u> |
| 10 | <u>20.0</u> |
| 11 | 22.8 |
| 12 | 24.8 |
| 13 | 27.9 |

Form 2 can also be characterized by a subset of these peaks, for example the peaks at 7.5, 19.3 and 20.0.

Form 3

Figure 4:
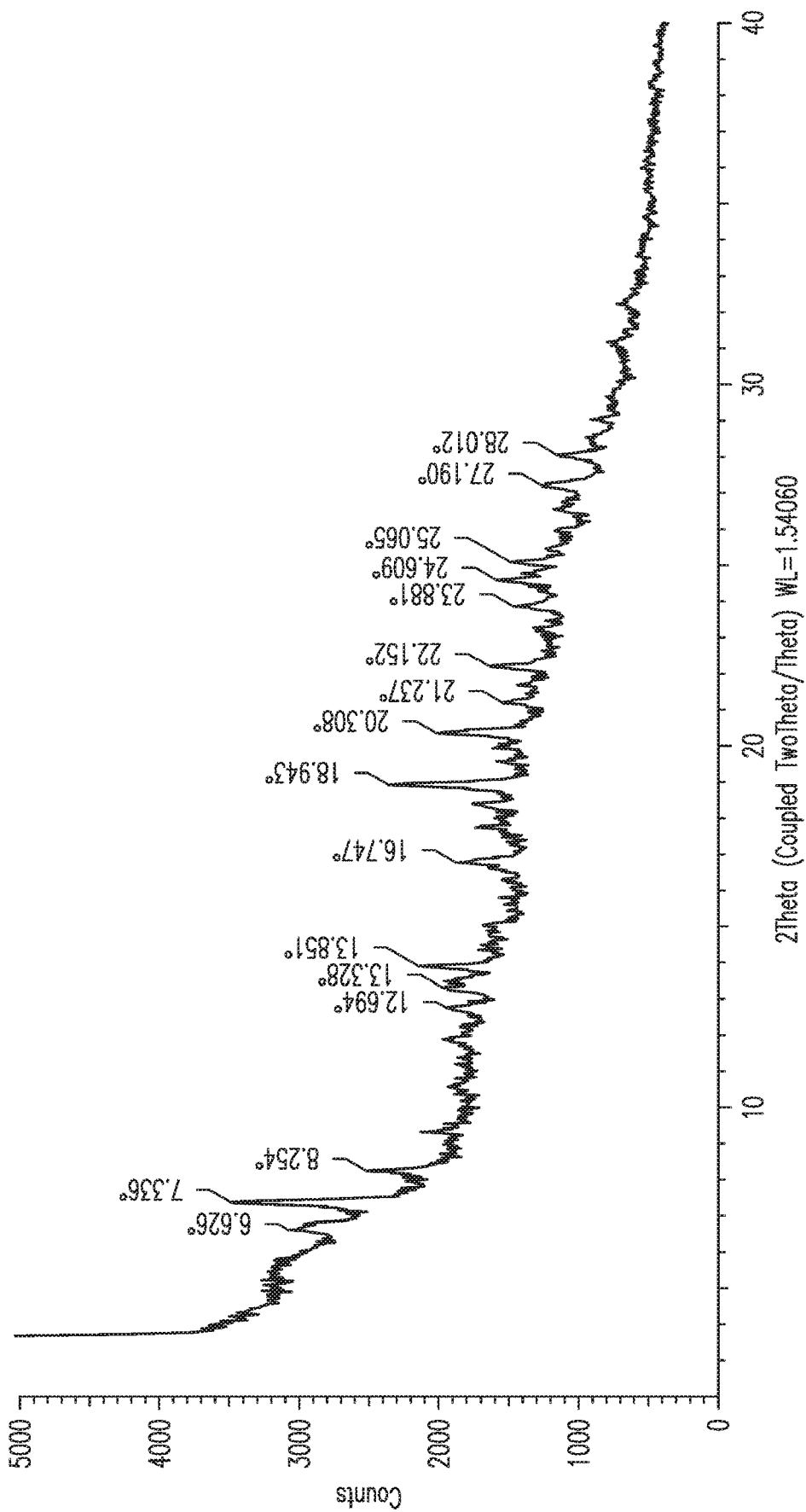
FIG. 4: X-ray powder diffraction pattern of Form 3.

Compound X of Form 1 was suspended in methanol and within a few minutes it evolved into a sticky solid product. The product exhibited the XRPD pattern shown in FIG. 4, and is referred to herein as Form 3. Note that a different form (Form 8) was obtained after longer stirring in methanol on a larger scale, as described below; thus Form 3 may be a transient form or a mixture formed as Form 1 evolves under these conditions.

| List 3: XRPD peak listing for Form 3 (2Theta: most intense peaks are underlined) ||
| --- | --- |
| 1 | 6.6 |
| 2 | <u>7.3</u> |
| 3 | 8.3 |
| 4 | 12.7 |
| 5 | 13.3 |
| 6 | <u>13.9</u> |
| 7 | <u>16.7</u> |
| 8 | <u>18.9</u> |
| 9 | <u>20.3</u> |
| 10 | <u>21.2</u> |
| 11 | 22.2 |
| 12 | 23.9 |
| 13 | <u>24.6</u> |
| 14 | 25.1 |
| 15 | 27.2 |
| 16 | 28.0 |

Form 3 can also be characterized by a subset of these peaks, for example the peaks at 7.3, 18.9 and 21.2.

Form 4

Figure 5:
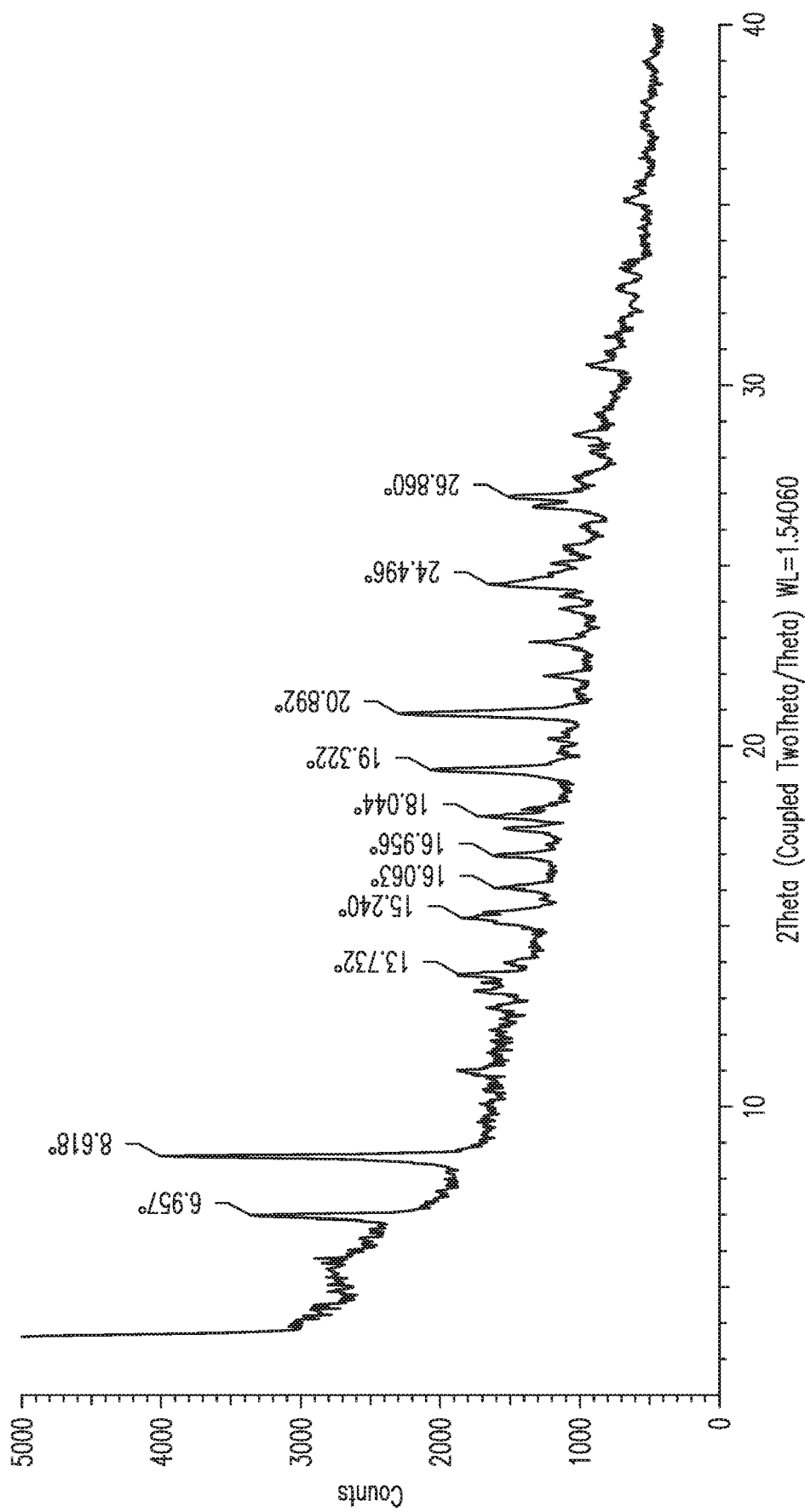
FIG. 5: X-ray powder diffraction pattern of Form 4.

Compound X of Form 1 (1.2 g) was suspended in water (12 mL) and stirred at 20° C. for 3 days. The product exhibited the XRPD pattern shown in FIG. 5, and is referred to herein as Form 4. The XRPD is from a sample dried with filter paper. The TGA analysis for Form 4 shows gradual loss of weight beginning about 40° C. and becoming rapid around 100° C., to a plateau at about 60% of original weight at 120-170° C. Above that temperature, a gradual loss of weight is seen. The early loss of mass is consistent with loss of water from Form 4, and with the DSC, which shows a strong endotherm in the same temperature range and a plateau at about 110-180° C. Similarly, the dynamic vapor sorption (DVS) analysis for Form 4 shows a rapid loss of about 20% of sample mass as relative humidity dropped to around 50%, after which cycling to lower then higher then lower and then higher relative humidity produced corresponding decrease, increase, decrease and increase of sample mass with a minimum mass about 65% of original, and maximum at about 80% of original mass. Form 4 is thus a hydrated form, and evolves depending on RH. The degree of hydration of the sample varies with relative humidity from an anhydrous form at very low humidity, to a trihydrate at RH about 20-50%, to a hexahydrate at RH above 60%. A sample of Form 4 dried at 0% relative humidity (RH) produces an XRPD consistent with Form 1.

| List 4: XRPD peak listing for Form 4 (2Theta: most intense peaks are underlined) | |
|---|---|
| 1 | 7.0 |
| 2 | 8.6 |
| 3 | 13.7 |
| 4 | 15.2 |
| 5 | 16.1 |
| 6 | 17.0 |
| 7 | 18.0 |
| 8 | 19.3 |
| 9 | 20.9 |
| 10 | 24.5 |
| 11 | 26.9 |

Form 4 can also be characterized by a subset of these peaks, for example the peaks at 7.0, 8.6, 19.3 and 20.9.

Form 5

Figure 6B:
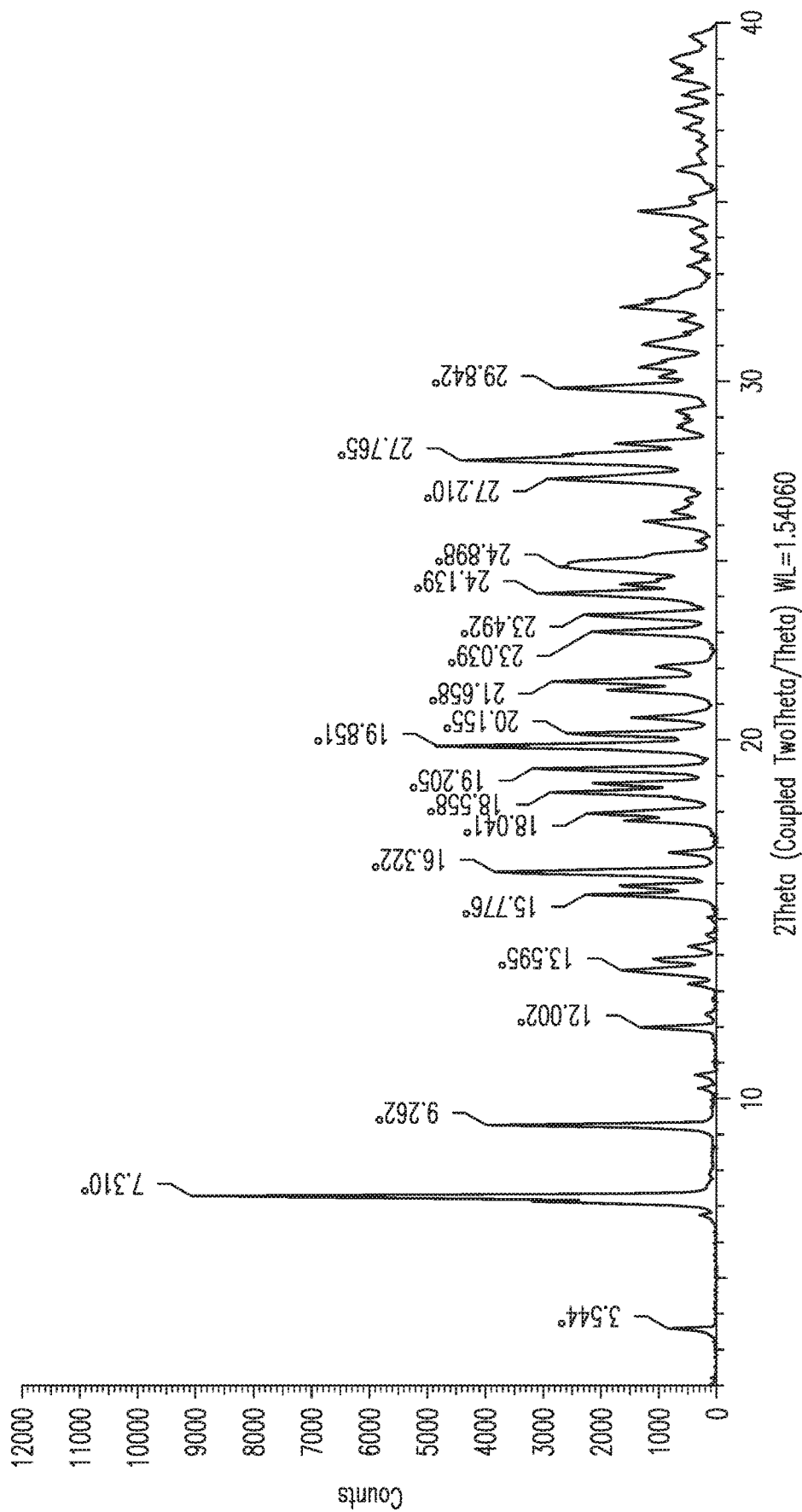
FIG. 6B: X-ray powder diffraction pattern of Form 5 from larger scale preparation.

A sample of Form 4 was dried under dry air flow for a day, giving a powder that exhibited the XRPD shown in FIG. 6A. This material is referred to herein as Form 5. The DSC for Form 5 shows a sharp exotherm at about 204° C., and the sample begins turning black at about this temperature, indicating decomposition. TGA shows about 7% loss of mass between 45° C. and 160° C. Karl Fisher analysis shows a water content of 9.6% for Form 5, corresponding to a trihydrate, but the sample appears to lose mass at RH below about 30%; and at RH above 80%, it converts to Form 4 within a day.

Forms 1, 4 and 5 of Compound X thus appear to interconvert as relative humidity is varied, and it may be a mixture of these hydrated forms. Form 5 is a preferred form for handling at ambient temperatures around 25° C. during manufacture, because it crystallizes as a well-behaved solid that is more stable during storage and handling than other forms, provided suitable relative humidity of around 20-50% RH, preferably 30-40%, is maintained. Within these RH ranges, the material is primarily trihydrate and is suitably well-behaved and stable for handling and storage without special precautions.

Larger Scale Preparation of Form 5

Water (20 mL) and THF (40 mL) were mixed in a flask, and Compound X (10 g, ca. 91% pure by HPLC) was added with stirring at 25° C. to provide a clear yellow solution. A 20 mg sample of Form 5 (see above) was added as a seed, and the mixture was stirred for 50 mins. THF (140 mL) was then added slowly, over 1 hr and the mixture was stirred for 2 hr more. The suspension was filtered, and the wet cake was washed with cold (<5° C.) water, then dried at 20-25° C. for 11 hrs at 100 mbar pressure, providing 6.6 g of Form 5 trihydrate that was 97.8% pure by HPLC. The sample produced the XRPD pattern shown in FIG. 6B. It appears stable when stored at 25-50% relative humidity, preferably 30-40% RH; at lower or higher relative humidity, it may evolve to different hydrated states as described herein. Over-drying produces a form that decomposed at room temperature within a few hours, further demonstrating the stability advantage of hydrated forms.

| List 5: XRPD peak listing for Form 5 (2Theta: most intense peaks are underlined) | |
|---|---|
| 1 | 7.3 |
| 2 | 9.3 |
| 3 | 12.0 |
| 4 | 13.6 |
| 5 | 15.8 |
| 6 | 16.3 |
| 7 | 18.0 |
| 8 | 18.6 |
| 9 | 19.2 |
| 10 | 19.9 |
| 11 | 20.2 |
| 12 | 21.7 |
| 13 | 23.0 |
| 14 | 23.5 |
| 15 | 24.1 |
| 16 | 24.9 |
| 17 | 27.3 |
| 18 | 27.8 |
| 19 | 29.8 |

Form 5 can also be characterized by a subset of these peaks, for example the peaks at 7.3, 9.3, and 27.8; and optionally by peaks at 7.3, 9.3, 19.9 and 27.8.

Form 5 (trihydrate) can alternatively be characterized by a single crystal X-ray structure that is monoclinic, space group P2(1), having unit cell dimensions a=13.121(4) Å; b=7.400(3) Å; c=25.017(8) Å ($\alpha$=90°; $\beta$=96.037°; $\gamma$=90°); and unit cell volume of 2415.6(14) Å$^3$. Data for this structure was collected at wavelength 1.54178 Å, 100° K; theta range 3.99° to 68.44°; 47822 reflections collected. The single crystal structure confirms the presence of three water molecules per molecule of Compound X in the unit cell, with the water molecule located in channels.

Form 6

Figure 7:
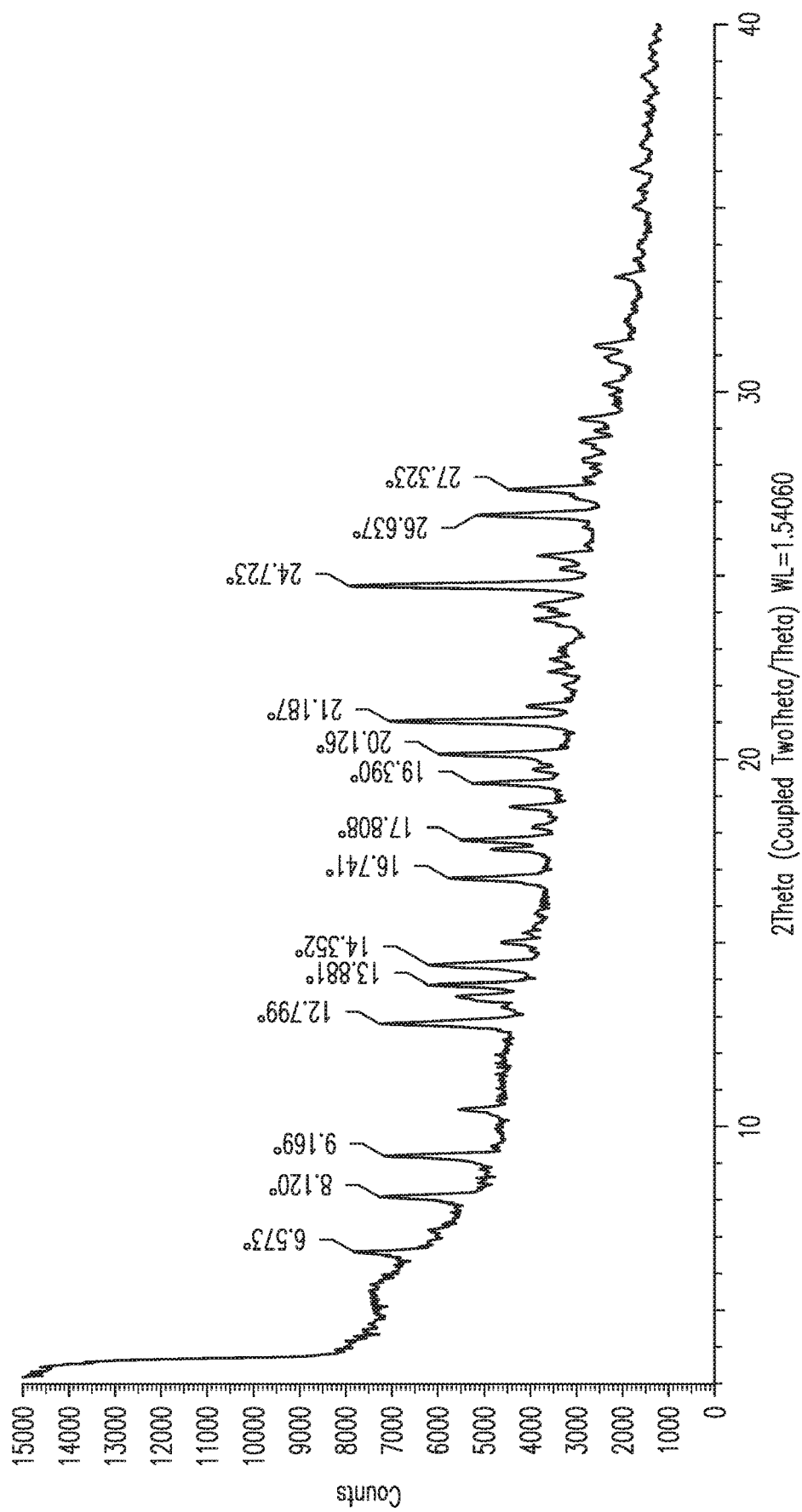
FIG. 7: X-ray powder diffraction pattern of Form 6.

Compound X of Form 1 (1.2 g) was suspended in DMSO: water (25:75 v/v ratio, 12 mL) and stirred at 20° C. for 3 days. A sample of the solid was collected and dried with filter paper. The product exhibited the XRPD pattern shown in FIG. 7, and is referred to herein as Form 6. DSC and TGA are consistent with loss of solvent up to about 130° C. and again between 150° C. and 200° C., followed by degradation above 200° C.

| List 6: XRPD peak listing for Form 6 (2Theta: most intense peaks are underlined) | |
|---|---|
| 1 | 6.6 |
| 2 | 8.1 |
| 3 | 9.2 |
| 4 | 12.8 |
| 5 | 13.9 |

| List 6: XRPD peak listing for Form 6 (2Theta: most intense peaks are underlined) | |
| --- | --- |
| 6 | <u>14.4</u> |
| 7 | <u>16.7</u> |
| 8 | 17.8 |
| 9 | 19.4 |
| 10 | <u>20.1</u> |
| 11 | <u>21.2</u> |
| 12 | <u>24.7</u> |
| 13 | <u>26.6</u> |
| 14 | 27.3 |

Form 6 can also be characterized by a subset of these peaks, for example the peaks at 8.1, 9.2, and 12.8; and optionally by additional peaks at 21.2 and 24.7.

Form 7

Figure 8:
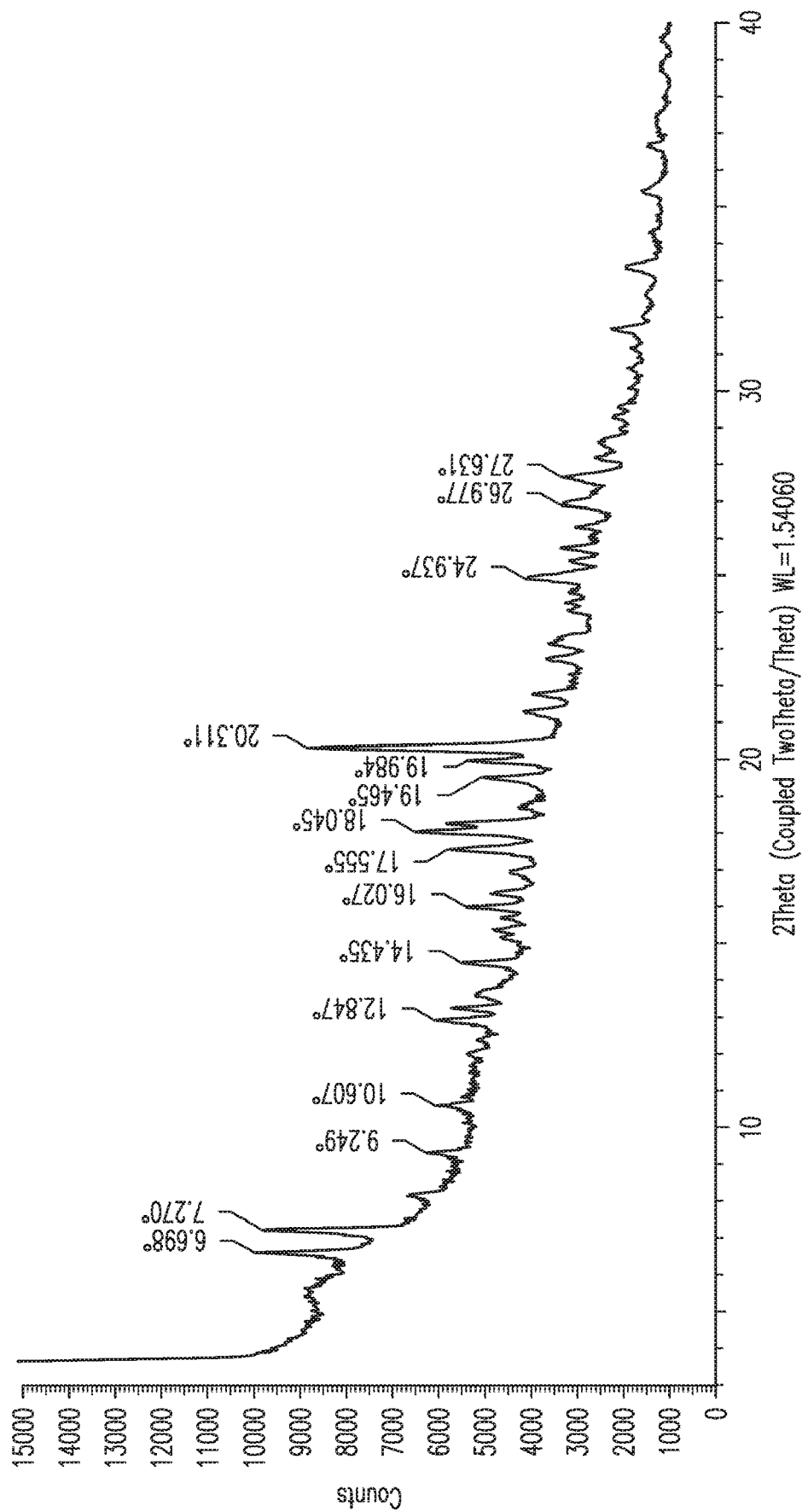
FIG. 8: X-ray powder diffraction pattern of Form 7.

Compound X of Form 6 made as described above was dried for a day under dry airflow. The resulting powder exhibited the XRPD pattern shown in FIG. 8, and is referred to herein as Form 7. DSC shows a large exotherm starting about 134° C. and continuing to about 170° C. $^1$H NMR shows about 2 equivalents of DMSO present and some water (3.6%). Karl Fisher titration confirms the presence of 3.6% water, corresponding to 1 equivalent. This form is thus a solvate.

| List 7: XRPD peak listing for Form 7 (2Theta: most intense peaks are underlined) | |
| --- | --- |
| 1 | <u>6.7</u> |
| 2 | <u>7.3</u> |
| 3 | 9.2 |
| 4 | 10.6 |
| 5 | 12.8 |
| 6 | 14.4 |
| 7 | 16.0 |
| 8 | <u>17.6</u> |
| 9 | <u>18.0</u> |
| 10 | 19.5 |
| 11 | 20.0 |
| 12 | <u>20.3</u> |
| 13 | <u>24.9</u> |
| 14 | 27.0 |
| 15 | 27.6 |

Form 7 can also be characterized by a subset of these peaks, for example the peaks at 6.7, 7.3 and 20.3.

Form 8

Figure 9:
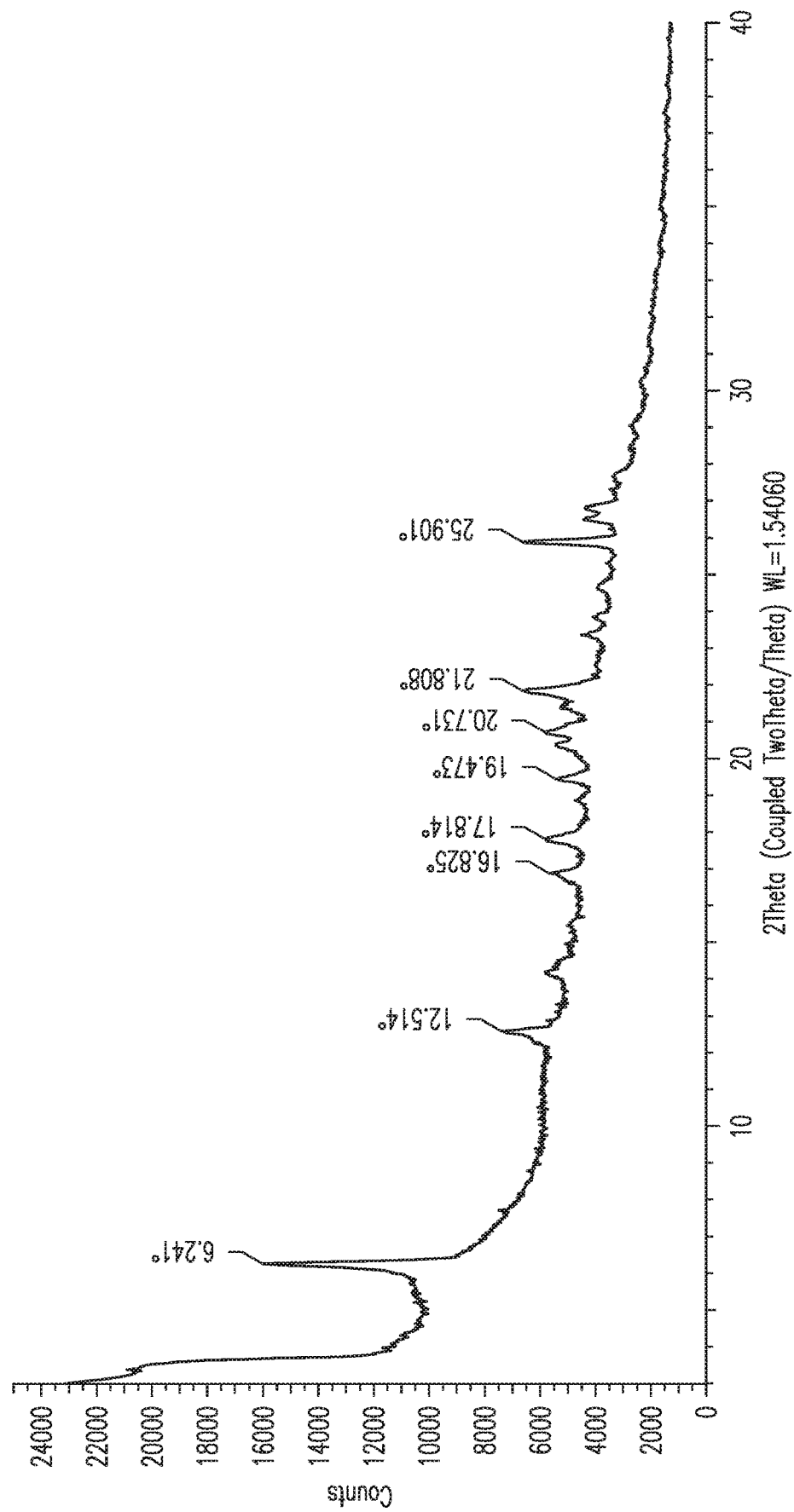
FIG. 9: X-ray powder diffraction pattern of Form 8.

Compound X of Form 1 (1.2 g) was suspended in methanol (12 mL) and stirred at 20° C. for 3 days. A sample of the solid was collected and produced the XRPD pattern shown in FIG. 9 (without drying), which is referred to herein as Form 8. When a sample of Form 8 was dried under dry air flow, the peaks broadened substantially but generally appear in about the same positions. TGA for the dried sample shows gradual loss of mass (about 4%) out to 140° C., and a sharper loss of mass beginning about 170° C. DSC shows a strong exotherm at about 172° C. that may be associated with degradation of the sample.

| List 8: XRPD peak listing for Form 8 (2Theta: most intense peaks are underlined) | |
| --- | --- |
| 1 | <u>6.2</u> |
| 2 | 12.5 |
| 3 | 16.8 |
| 4 | <u>17.8</u> |
| 5 | 19.5 |
| 6 | <u>20.7</u> |
| 7 | <u>21.8</u> |
| 8 | <u>25.9</u> |

Form 8 can also be characterized by a subset of these peaks, for example the peaks at 6.2, 21.8 and 25.9.

Form 9

Figure 10:
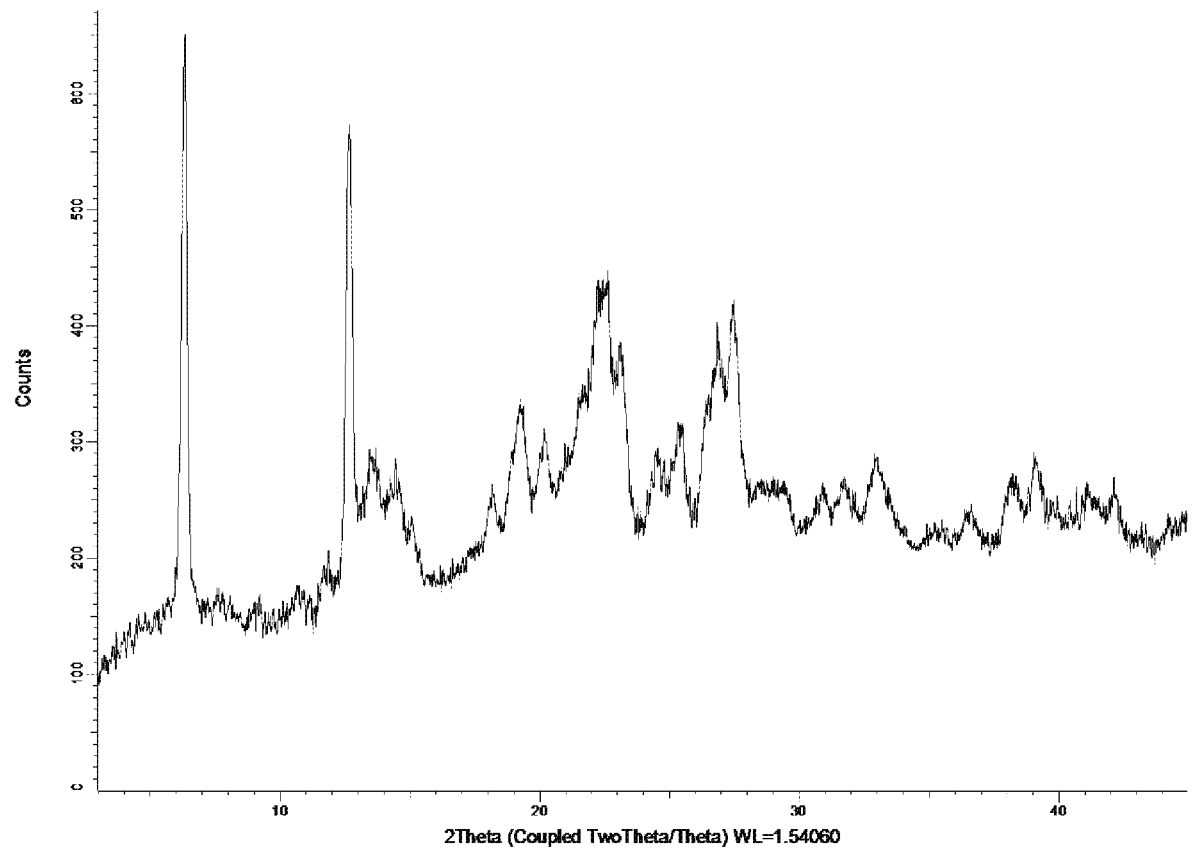
FIG. 10: X-ray powder diffraction pattern of Form 9.

Compound X of Form 3 was suspended in acetone and water at 25° C. to 40° C. The ratio of water to acetone was varied from 2:98 to 10:90. After equilibration for 24 hours, a low-crystallinity hetero-solvate form was obtained in each case. While the XRPD varied with the proportion of water to acetone, all samples produced XRPD spectra with broad humps rather than sharp peaks. FIG. 10 shows the XRPD for a sample equilibrated in 10:90 water/acetone at 40° C. for 24 hours, and the following table summarizes the XRPD data for this sample. This solid form is referred to herein as Form 9.

| Angle °2θ | d value Å | Rel. intensity | Intensity description |
| --- | --- | --- | --- |
| 6.263687 | 14.09934 | 100.0% | strong |
| 11.86655 | 7.451857 | 11.9% | weak |
| 12.42631 | 7.117408 | 17.4% | weak |
| 12.61893 | 7.009192 | 91.6% | strong |
| 12.63825 | 6.998521 | 94.2% | strong |
| 13.42144 | 6.591842 | 21.0% | medium |
| 14.4584 | 6.121322 | 23.6% | medium |
| 19.28026 | 4.599924 | 23.3% | medium |
| 20.21352 | 4.389602 | 15.3% | weak |
| 22.13261 | 4.013133 | 38.6% | medium |
| 22.32398 | 3.979161 | 45.7% | medium |
| 23.14303 | 3.840154 | 35.3% | medium |
| 24.56875 | 3.620444 | 13.9% | weak |
| 25.45017 | 3.49702 | 17.2% | weak |
| 26.95376 | 3.305257 | 30.7% | medium |
| 27.52409 | 3.23805 | 35.9% | medium |
| 33.01997 | 2.710583 | 12.5% | weak |
| 39.13803 | 2.299801 | 11.5% | weak |

Form 9 can be characterized by a subset of these peaks, for example the peaks identified in the table above as 'strong' relative intensity, e.g. peaks at 6.3 and 12.6 and optionally one or more of the peaks in the table having medium relative intensity, such as peaks at 22.1, 22.3, 23.1, 27.0 and 27.5

Form 10

Compound X of Form 1 (anhydrate) was exposed to 43% relative humidity for one day or more. The crystalline product appears to be a sesquihydrate (Compound X-1.5 H$_2$O) based on water content determination. Note that Form 5, the trihydrate, under similar conditions would be stable, yet when starting with the anhydrate, it appears to equilibrate as a sequihydrate under these conditions and remains in that form for at least 14 days when kept at the same relative humidity. This crystalline form produces the XRPD spectrum shown in FIG. 11, and is referred to herein as Form 10. The table below summarizes the main peaks in the XRPD of this sample.

| Angle °2θ | d value Å | Rel. intensity | Intensity description |
|---|---|---|---|
| 6.614136 | 13.35305 | 54.0% | medium |
| 7.75259 | 11.39455 | 14.9% | weak |
| 11.04603 | 8.003481 | 88.8% | strong |
| 13.25272 | 6.675381 | 33.7% | medium |
| 15.63391 | 5.663605 | 25.2% | medium |
| 16.49456 | 5.369978 | 100.0% | strong |
| 17.94729 | 4.93845 | 17.1% | weak |
| 18.62139 | 4.761168 | 23.3% | medium |
| 19.39448 | 4.573091 | 17.4% | weak |
| 20.28656 | 4.373962 | 10.7% | weak |
| 22.23199 | 3.995416 | 44.1% | medium |
| 23.39858 | 3.798789 | 41.6% | medium |
| 24.7725 | 3.591125 | 17.5% | weak |
| 27.42817 | 3.249156 | 34.8% | medium |
| 30.97646 | 2.884582 | 10.5% | weak |
| 31.35952 | 2.850214 | 7.6% | weak |
| 33.26275 | 2.691351 | 6.5% | weak |
| 34.28825 | 2.613168 | 4.3% | weak |
| 35.97828 | 2.494198 | 4.5% | weak |
| 37.32749 | 2.407085 | 3.2% | weak |
| 38.84248 | 2.316617 | 6.5% | weak |

Form 10 can be characterized by the XRPD peaks in the above table having medium to strong relative intensities, e.g. peaks at 6.6, 11.0, 13.3, 15.6, 16.5, 18.6, 22.2, 23.4 and 27.4. It can also be characterized by a subset of these peaks, for example the peaks having relative intensity of 40 or higher, e.g. peaks at 6.6, 11.0, 16.5, 22.2, and 23.4, or by a subset of at least 3 or 4 of these peaks.

Form 11

Figure 12:
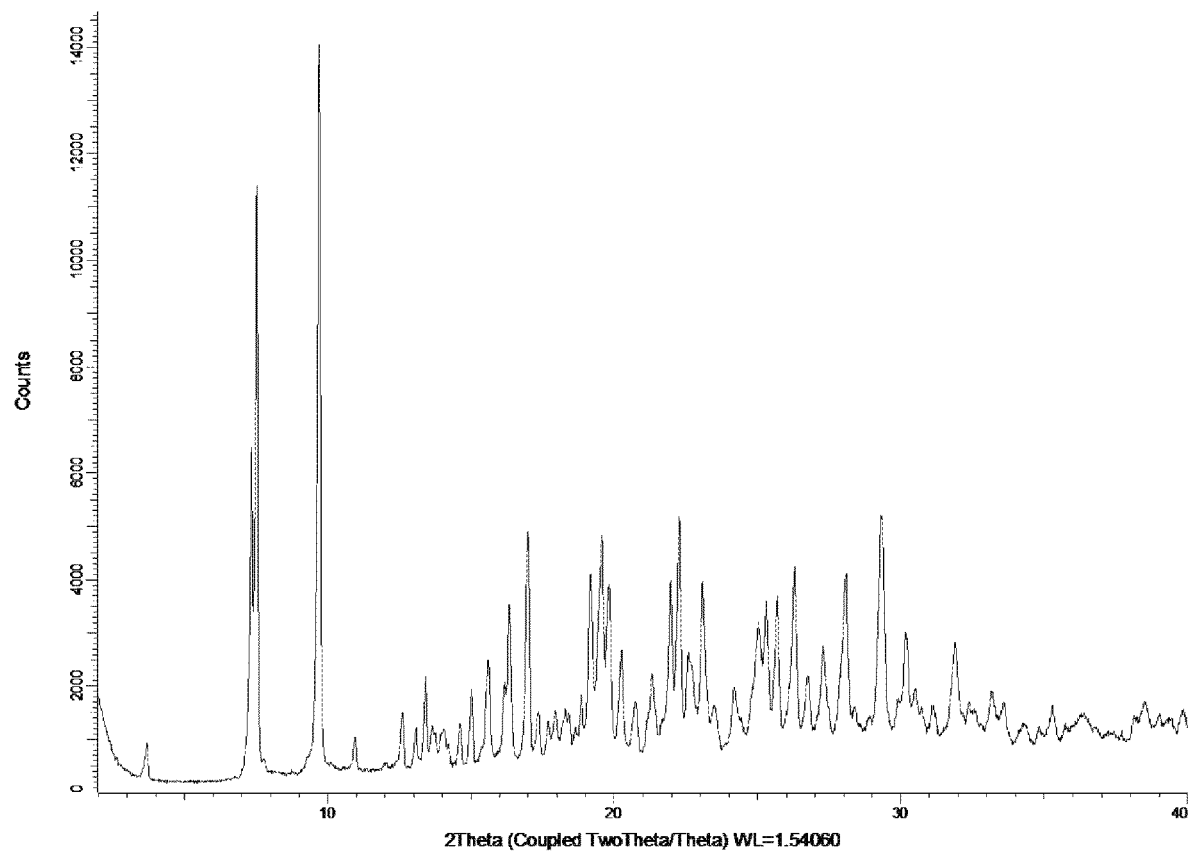
FIG. 12: X-ray powder diffraction pattern of Form 11.

Compound X of Form 5, the trihydrate, was exposed to relative humidity of 22% for about 3 days to provide a crystalline solid characterized as a dihydrate (Compound X-2H$_2$O) based on water content analysis. This material readily reverts to the trihydrate (Form 5) if exposed to relative humidity above about 40%. The dihydrate, referred to herein as Form 11, produced the XRPD spectrum shown in FIG. 12: the main peaks in that XRPD spectrum are listed in the following table.

| Angle °2θ | d value Å | Rel. intensity | Intensity description |
|---|---|---|---|
| 3.571943 | 24.71601 | 1.5% | weak |
| 7.436401 | 11.87831 | 35.5% | medium |
| 9.691609 | 9.118732 | 100.0% | strong |
| 15.62894 | 5.665396 | 15.8% | weak |
| 16.27854 | 5.440749 | 13.8% | weak |
| 17.03032 | 5.20223 | 26.8% | medium |
| 19.52173 | 4.543567 | 28.0% | medium |
| 20.30047 | 4.370997 | 12.2% | weak |
| 22.21399 | 3.998612 | 26.5% | medium |
| 25.2108 | 3.529677 | 14.4% | weak |
| 25.26935 | 3.521632 | 20.2% | medium |
| 26.31417 | 3.384125 | 26.2% | medium |
| 27.24226 | 3.270906 | 11.1% | weak |
| 28.06091 | 3.177313 | 25.0% | medium |
| 29.32342 | 3.043323 | 34.3% | medium |
| 30.2374 | 2.953383 | 14.5% | weak |
| 31.95423 | 2.798512 | 13.9% | weak |
| 32.37313 | 2.76325 | 5.1% | weak |
| 33.33318 | 2.685825 | 4.2% | weak |
| 35.18906 | 2.548309 | 3.3% | weak |
| 36.32229 | 2.471361 | 3.8% | weak |
| 38.46064 | 2.338733 | 5.4% | weak |

Form 11 is characterized by the XRPD peaks in this table having relative intensities of 20 or higher, or alternatively those peaks having relative intensity of at least 25, e.g., peaks at 7.4, 9.7, 17.0, 19.5, 22.2, 26.3, 28.1, and 29.3, or a subset of 3, 4 or 5 of these peaks having relative intensity of at least 26 or at least 28 in the table.

Form 12

Figure 13:
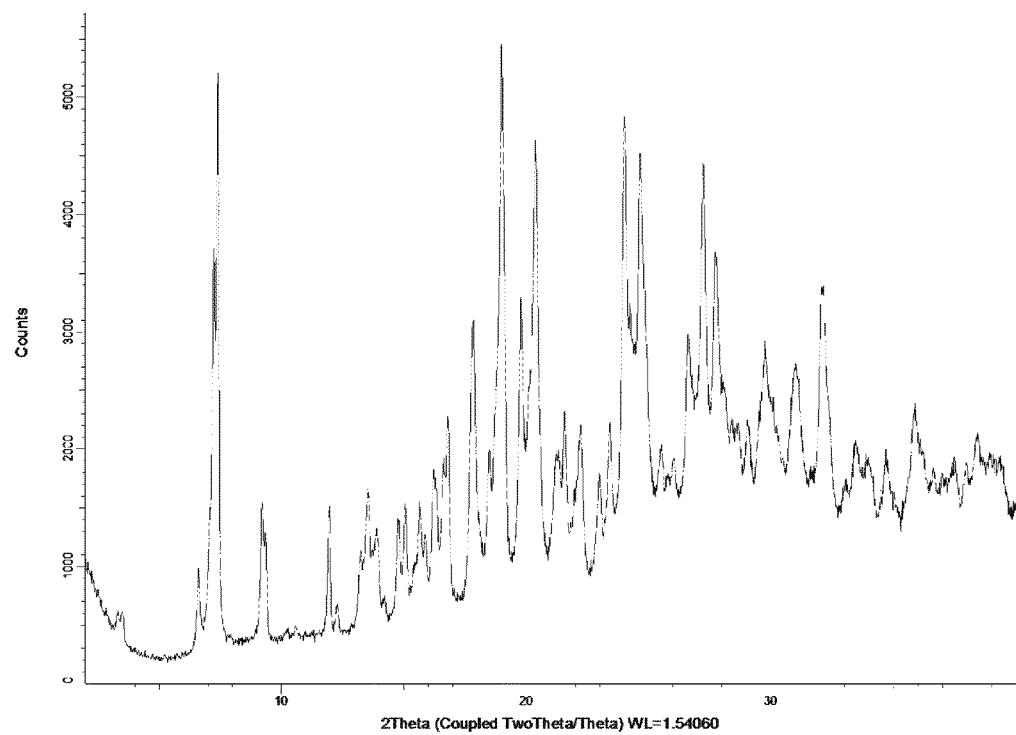
FIG. 13: X-ray powder diffraction pattern of Form 12.

Compound X of Form 5 was exposed to air with a relative humidity of 65% for about 3 days, providing a crystalline material characterized as a tetra-hydrate based on water content analysis. This material readily reverts to the trihydrate (Form 5) if the relative humidity is reduced to about 40%. The tetrahydrate, referred to herein as Form 12, produced the XRPD spectrum shown in FIG. 13: the main peaks in that XRPD spectrum are listed in the following table.

| Angle °2θ | d value Å | Rel. intensity | Intensity description |
|---|---|---|---|
| 6.631469 | 13.31819 | 15.1% | weak |
| 7.33743 | 12.0383 | 72.0% | strong |
| 9.266574 | 9.536012 | 20.4% | medium |
| 11.93609 | 7.408599 | 22.6% | medium |
| 13.52676 | 6.540754 | 24.4% | medium |
| 13.84431 | 6.391434 | 16.2% | weak |
| 14.79842 | 5.98143 | 17.5% | weak |
| 15.04928 | 5.882283 | 20.4% | medium |
| 15.66726 | 5.651626 | 17.4% | weak |
| 16.26423 | 5.445504 | 22.3% | medium |
| 16.73753 | 5.292569 | 26.6% | medium |
| 17.82639 | 4.971669 | 51.5% | medium |
| 18.53134 | 4.784101 | 23.2% | medium |
| 19.00545 | 4.665812 | 100.0% | strong |
| 19.80871 | 4.478384 | 49.8% | medium |
| 20.37349 | 4.355495 | 82.5% | strong |
| 21.28466 | 4.171054 | 21.3% | medium |
| 21.54339 | 4.121543 | 27.1% | medium |
| 22.20079 | 4.000961 | 25.6% | medium |
| 22.99691 | 3.864222 | 17.5% | weak |
| 23.42381 | 3.794754 | 25.5% | medium |
| 24.03782 | 3.699195 | 80.9% | strong |
| 24.68722 | 3.603338 | 73.6% | strong |
| 24.89251 | 3.574084 | 40.2% | medium |
| 25.51126 | 3.488783 | 15.7% | weak |
| 26.01732 | 3.42206 | 13.3% | weak |
| 26.66767 | 3.340063 | 33.5% | medium |
| 27.24035 | 3.27113 | 67.3% | strong |
| 27.76732 | 3.210236 | 50.0% | medium |
| 28.03201 | 3.180522 | 23.7% | medium |
| 28.61161 | 3.117397 | 17.1% | weak |
| 29.06848 | 3.069431 | 17.4% | weak |
| 29.78494 | 2.997208 | 28.9% | medium |
| 31.00716 | 2.881796 | 27.2% | medium |
| 32.11536 | 2.784838 | 42.0% | medium |
| 33.47732 | 2.67459 | 13.0% | weak |
| 35.87286 | 2.501286 | 20.9% | medium |

Form 12 can be characterized by XRPD peaks having a relative intensity of at least 40 in the table above, i.e. XRPD peaks at 7.3, 17.8, 19.0, 19.8, 20.4, 24.0, 24.7, 24.9, 27.2, 27.8 and 32.1. Alternatively, it can be characterized by a subset of at least 3, or at least 4, or at least 5 of these peaks. Form 12 can also be characterized by the XRPD peaks described as strong relative intensity in the table, i.e., peaks at 7.3, 19.0, 20.4, 24.0, 24.7, and 27.2.

Samples of the hydrates of Compound X, including Forms 5, 11 and 12 were shown to interconvert readily as the relative humidity was varied from about 22% to about 92%. Note that at 92% relative humidity, Compound X appears to be a mixture of a crystal form characterized as hexahydrate mixed with the tetrahydrate of Form 12. By comparison, the anhydrate (Form 1) preferentially converts to a sesquihydrate as the relative humidity is increased to 43%, and evolves to trihydrate and tetrahydrate at higher relative humidities.

Pharmaceutical Compositions of Compound X

Compound X (500 mg) and L-arginine (332.5 mg) are combined in a vial. Saccharose (crystalline, pyrogen-free sucrose: 1000 mg) is added along with water suitable for injection (8.00 mL). The pH of the solution is adjusted, if necessary, using 1.0N HCl or 1.0N NaOH to arrive at a pH of 5.0±0.5, preferably a pH of 5.0±0.2. This provides a solution containing about 62.5 mg/mL of Compound X as an arginine salt. This solution can be filtered if necessary, and can be lyophilized to provide a white or off-white solid (lyophilizate). The lyophilized solid can be reconstituted with sterile water or a pharmaceutically acceptable aqueous carrier such as isotonic saline or dextrose to provide a solution suitable for intravenous administration. The lyophilizate should be stored in a container that excludes light to protect the lyophilizate from photodegradation. This process can be scaled up or down to provide unit dosages for storage and distribution, or bulk material that can be further processed as desired. For scale-up, temperature control is important: Compound X in solution should be maintained at a temperature below 10° C., preferably between 0° C. and 8° C., and more preferably between 2° C. and 8° C., prior to addition of arginine or other base, as the compound is subject to hydrolytic degradation in water in the absence of a base or outside the pH range of 4-6.

In one embodiment, a mixture according to the above example is prepared as described using the trihydrate (Form 5) of Compound X in an amount that contains about 500 mg of Compound X anhydrous, and is lyophilized in a vial that is then sealed for storage and distribution, preferably using a butyl rubber stopper (e.g., D777 stopper), where the lyophilizate in each vial contains about 500 mg of Compound X. The vials of lyophilizate are stored at or below room temperature until use.

An alternative formulation suitable for IV injection contains Compound X (100 mg) and 0.5N Sodium bicarbonate (0.75 mL), and pH adjuster if necessary (1 N NaOH or 1 N HCl as needed) to bring the pH to about 5.5 (between pH 5 and pH 6), plus an amount of water for injection sufficient to achieve a final concentration of 100 mg/ml.

Stability of Compound X

Compound X is stable in solid form, but salts of Compound X are more stable in solution than the free acid; thus it became important to identify suitable pharmaceutically acceptable salts to use for administration. Salts of Compound X were prepared by adding a base (1.0 or 2.0 equiv.) to Compound X in water, and lyophilizing the solution. The solids thus obtained appear to be amorphous by XRPD. In this manner, formation of salts of Compound X were attempted with sodium hydroxide, (L)-lysine, (L)-arginine, calcium hydroxide, meglumine, and magnesium hydroxide. The sodium salts and the arginine salts were found to be particularly stable and thus desirable as forms for administration in aqueous media typically used for intravenous injections and infusions.

Samples of the disodium salt and the di-(L)-arginine salt as solids were subjected to stability testing at 25° C. and 40° C. The sample of sodium salt was 97.2% pure by HPLC initially, and after 6 weeks at 25° C., it was still 96.2% pure. The same material held at 40° C. was 94.8% pure after 3 weeks, and 93.6% pure after 6 weeks. Significant impurities that appear or increase during the study appear at relative retention times (RRT) 0.34 and 1.11 (with Compound X defined as RRT=1).

Figure 11:
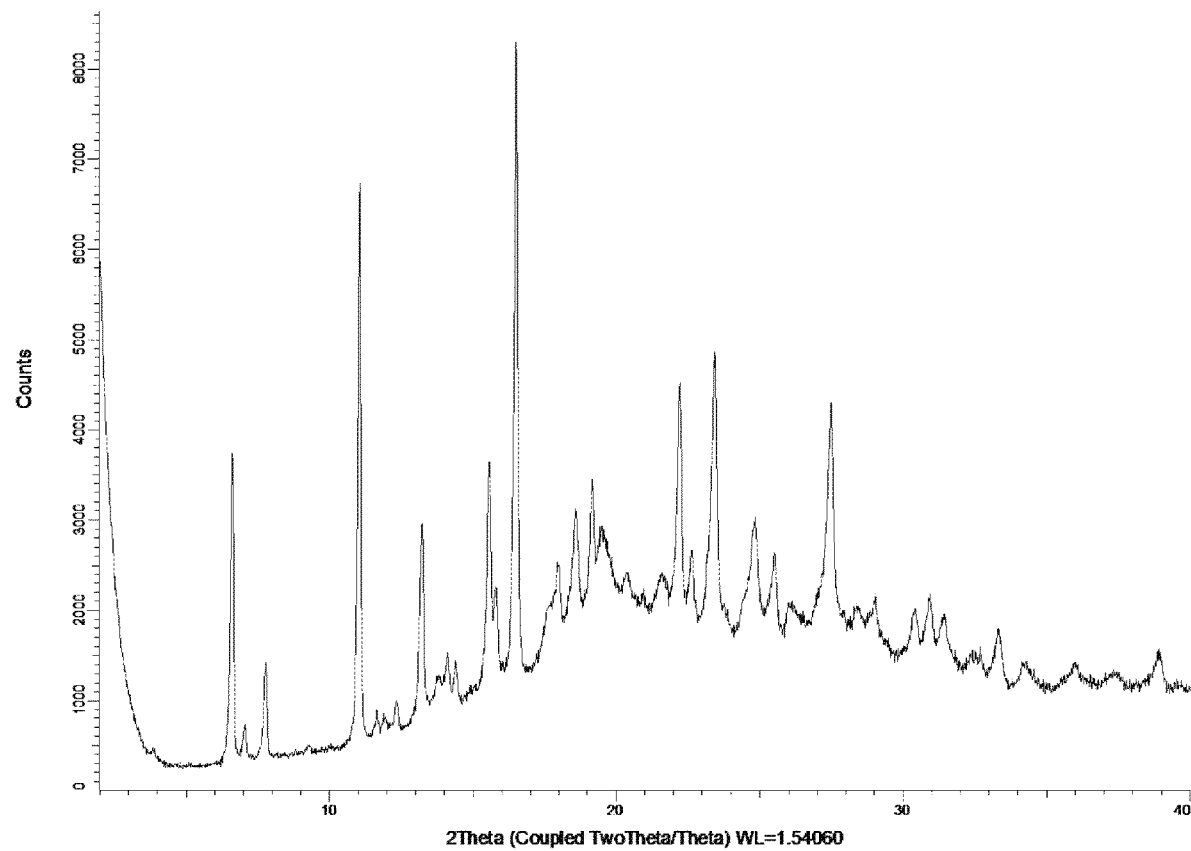
FIG. 11: X-ray powder diffraction pattern of Form 10.

The arginine salt was 97.3% pure by HPLC initially, and was 96.3% pure after 6 weeks at 25° C. At 40° C., its purity dropped to 95.1% after 3 weeks and 94.2% after 6 weeks. Significant impurities that appear or increase during this study appear at relative retention times (RRT) 1.09, 1.11 and 1.13 (with Compound X defined as RRT=1). The HPLC traces for the samples from these stability studies after 6 weeks at 25° C. and 40° C. respectively are shown in FIGS. 10 and 11. The lower trace in each Figure is a sample used to measure the limit of quantitation (LOQ); the next trace above that represents the sample of Compound X used for salt formation; the next trace above that one is for the arginine salt after 6 weeks; and the next (top) trace is for the sodium salt after 6 weeks.

HPLC Conditions for the stability studies (FIGS. 10 and 11):
Agilent 1290 system with UV detector at 260 nm
Acquity HSS T3 column, 100 mm×2.1 mm ID; 1.8 µm particle size (supplied by Waters)
Column temp: 40° C.
Mobile phases
   A: 0.05% TFA in water
   B: 0.05% TFA in methanol
Flow rate: 0.45 mL/min
Gradient (A/B ratio): 97:3 for 8 minutes; 75:25 for 3 minutes; 0:100 for 1 minute Compound X was also found to degrade photochemically; thus Compound X should be stored in dark or opaque containers for best shelf life. In one embodiment of the invention, Compound X is packaged in a container that substantially reduces exposure to light, preferably in an atmosphere at a relative humidity of 25-50% humidity and more preferably at a relative humidity of 30-40% or 30-45%.

Biological Activity

Bacterial Screens and Cultures

Bacterial isolates were cultivated from −70° C. frozen stocks by two consecutive overnight passages at 35° C. in ambient air on 5% blood agar (Remel, Lenexa, Kans.). Quality control and *P. aeruginosa* ATCC 27853) is from the American Type Culture Collection (ATCC; Rockville, Md.) and PAO1 was received from Dr. K. Poole.

Construction of *Escherichia coli* Isogenic Strains Strains NB27273-CDY0026 (Parent), NB27273-CDY0033 (KPC2) and NB27273-CDY0030 (SHV12)

Strain NB27273 (BW25113 pspB::Km$^r$) was obtained from the Keio transposon insertion collection. The strain has the pspB gene replaced by a kanamycin resistance marker (BW25113 pspB::Km$^r$). This strain was cured of the transposon in pspB via FLP recombinase using published methodology. The resulting strain, BW25113 pspB, was used as a host for multicopy vectors expressing key β-lactamases. Multicopy plasmids directing constitutive expression of β-lactamases were established as follows: Synthetic, codon optimized genes encoding *E. coli* KPC2 and SHV12-lactamases were made by DNA2.0 (Palo Alto, Calif.). Each of the synthetic fragments were designed to contain NotI and NcoI restriction sites at their termini, allowing ligation into a NotI/NcoI digested pET28a(+) derivative for protein expression. The inserts in these vectors served as template DNA for PCR amplification of the gene encoding KPC2 and SHV12, using primer pairs E225 (tcgcCTCGAGgcgactgcgctgacgaatttgg) (SEQ ID NO:1) and E202 (aatcGAATTCttactgaccattaacgcccaagc) (SEQ ID NO:2) and E227 (tcgcCTCGAGgcgagcccgcaaccgctgga) (SEQ ID NO:3) and E204 (aatcGAATTCttaacgctgccagtgctcaatc) (SEQ ID NO:4), respectively. The codon optimized nucleotide sequences and relevant primer recognition information is shown below:

```
SHV12
                                   (SEQ ID NO: 5)
ATGGGCCATCATCATCATCATCACAGCAGCGGCCTGGAAGTTCTGTTCCA

GGGGCCCGCGAGCCCGCAACCGCTGGAGCAGATCAAGCAGTCTGAGAGCC

AGCTGAGCGGCCGTGTGGGTATGATCGAGATGGATCTGGCTTCCGGCCGT
```

-continued

ACGCTGACGGCATGGCGTGCCGACGAACGTTTCCCGATGATGTCGACCTT

TAAAGTTGTTCTGTGTGGTGCGGTCTTGGCACGTGTAGACGCGGGTGACG

AACAACTGGAGCGCAAGATCCATTACCGCCAACAGGACTTGGTCGACTAC

AGCCCGGTTAGCGAAAAGCACCTGGCGGATGGCATGACCGTGGGTGAATT

GTGCGCCGCTGCGATTACCATGAGCGACAATAGCGCGGCTAATCTGCTGT

TGGCGACCGTTGGTGGCCCAGCGGGCTTGACCGCATTTCTGCGTCAAATC

GGCGATAATGTTACGCGTCTGGATCGCTGGGAAACGGAGCTGAACGAGGC

ACTGCCGGGTGATGCCCGTGATACCACGACTCCTGCTAGCATGGCAGCGA

CCCTGCGTAAACTGCTGACCAGCCAGCGTCTGAGCGCACGTAGCCAACGC

CAGCTGCTGCAATGGATGGTGGATGACCGCGTGGCGGGTCCGCTGATCCG

CTCCGTCCTGCCAGCAGGCTGGTTCATTGCGGACAAAACTGGTGCCTCTA

AGCGTGGTGCGCGTGGTATCGTCGCGCTGCTGGGTCCGAACAACAAAGCC

GAACGTATTGTGGTTATCTATCTGCGCGACACCCCGGCAAGCATGGCCGA

GCGCAACCAGCAAATTGCGGGCATTGGTGCGGCACTGATTGAGCACTGGC

AGCGTTAACGCCGGCG

E227

(SEQ ID NO: 6)

TCGCCTCGAGGCGAGCCCGCAACCGCTGGA

E204

(SEQ ID NO: 7)

AATCGAATTCTTAACGCTGCCAGTGCTCAATC

REV. COMP. E204

(SEQ ID NO: 8)

GATTGAGCACTGGCAGCGTTAAGAATTCGATT

KPC2

(SEQ ID NO: 9)

ATGGGCCATCATCATCATCATCACAGCAGCGGCCTGGAAGTTCTGTTCCA

GGGGCCCGCGACTGCGCTGACGAATTTGGTGGCCGAGCCGTTCGCGAAAT

TGGAGCAAGATTTTGGTGGTTCGATCGGTGTCTACGCGATGGACACCGGT

AGCGGTGCCACCGTGAGCTACCGTGCCGAAGAGCGTTTTCCGCTGTGTAG

CTCTTTCAAGGGTTTTCTGGCCGCAGCCGTGCTGGCACGCAGCCAACAGC

AAGCGGGCCTGCTGGACACCCCGATCCGTTACGGCAAAAATGCGCTGGTT

CCGTGGAGCCCGATTAGCGAAAAGTACCTGACCACCGGCATGACGGTGGC

GGAGTTGAGCGCTGCGGCGGTTCAGTATTCCGATAACGCTGCGGCAAATC

TGCTGCTGAAAGAACTGGGCGGTCCAGCGGGTCTGACGGCTTTCATGCGT

TCTATTGGCGACACCACCTTTCGCTTGGACCGCTGGGAGCTGGAGCTGAA

CAGCGCGATTCCGGGCGACGCACGTGATACGAGCAGCCCGCGTGCAGTGA

CCGAGAGCCTGCAGAAGCTGACCCTGGGCAGCGCACTGGCCGCACCGCAG

CGCCAACAGTTCGTCGATTGGCTGAAGGGTAACACCACCGGTAACCATCG

TATTCGCGCAGCGGTCCCGGCTGATTGGGCAGTTGGTGACAAGACTGGTA

CGTGCGGCGTTTATGGTACGGCGAATGACTACGCGGTTGTTTGGCCTACG

GGTCGTGCGCCGATCGTCCTGGCGGTGTATACCCGTGCTCCGAACAAAGA

CGATAAACACTCCGAAGCGGTCATCGCCGCAGCAGCGCGTCTGGCCCTGG

AAGGCTTGGGCGTTAATGGTCAGTAACGCCGGCG

E225

(SEQ ID NO: 10)

TCGCCTCGAGGCGACTGCGCTGACGAATTTGG

E202

(SEQ ID NO: 11)

AATCGAATTCTTACTGACCATTAACGCCCAAGC

REV. COMP. E202

(SEQ ID NO: 12)

GCTTGGGCGTTAATGGTCAGTAAGAATTCGATT
UNDERLINED = DNA ENCODING BL

The PCR products were then digested with XhoI and EcoRI and ligated into similarly digested plasmid pAH63-pstS(BlaP). Plasmid pAH63-pstS(BlaP) is a derivative of plasmid pAH63 (J Bacteriol: 183(21): 6384-6393) made by cloning the TEM-1 (bla) promoter and signal peptide encoding region from plasmid pBAD (J Bacteriol. 1995 July 177(14):4121-30) into plasmid pAH63. This fragment was PCR amplified from pBAD using primer pair E192 (ttcaCTGCAGtgaacgttgcgaagcaacggC) (SEQ ID NO:13) and E194 (TCGAggatcctcgagagcaaaaacaggaaggcaaaatgccg) (SEQ ID NO:14), digested with PstI and BamHI, and inserted into similarly digested plasmid pAH63. Therefore, expression of β-lactamases from pAH63-pstS(BlaP) based constructs is constitutive and the signal sequence is provided to direct these proteins to the periplasm. Plasmid pAH63 based vectors are used for insertion into the genome in single copy, however, to provide higher expression levels to allow more sensitive detection of the susceptibility of compounds to the β-lactamases, the expression inserts contained in these vectors were moved to the replicative multicopy vector pBAD-Kan (J Bacteriol. 1995 July 177(14):4121-30). To accomplish this, the inserts encompassing the β-lactamase genes, with the associated TEM promoter and signal sequences, were PCR amplified from their corresponding vectors using primer E269 (ccgTCTAGAcggatggcctttttgcgtttc) (SEQ ID NO:15) and E202 (aatcGAAT-TCttactgaccattaacgcccaagc) (SEQ ID NO:16) for the KPC2 construct and E204 (aatcGAATTCttaacgctgccagtgctcaatc) (SEQ ID NO:17) for the SHV12 construct. These fragments were then digested with XbaI and EcoRI, and each was inserted into pBAD18-kan that had been digested with the same enzymes to generate a pair of multicopy vectors expressing KPC2 and SHV12 respectively. These vectors were transformed into BW25113 pspB to generate strains NB27273-CDY0033 (expressing KPC2) and NB27273-CDY0030 (expressing SHV12). The pBAD18-kan vector also contains the TEM promoter region and signal sequence, (but lacks any intact β-lactamase genes) and was transformed into BW25113 pspB using standard protocols to generate the control strain NB27273-CDY0026. Expression of the β-lactamases was confirmed by verifying decreased susceptibility to example test antibiotics that are known substrates of KPC2 or SHV12.

Susceptibility Testing

Minimal Inhibitory Concentrations (MICs) were determined by the broth microdilution method in accordance with Clinical and Laboratories Institute (CLSI) guidelines. In brief, fresh overnight bacterial cultures were suspended in sterile saline, and adjusted to a 0.5 McFarland turbidity standard. Bacterial suspensions were then diluted in cation adjusted Mueller-Hinton Broth (MHB II; BBL) to yield a final inoculum of approximately $5\times10^5$ colony-forming units (CFU)/mL. A master plate of antibiotics was prepared at a concentration equivalent to hundred-fold the highest desired final concentration in 100% dimethyl sulfoxide (DMSO).

The master antibiotic plate was then diluted by serial two-fold dilution with a multichannel pipette. The resulting dilution series of compounds were diluted 1:10 with sterile water leading to a 10% DMSO final concentration. A volume of 10 μL of the drug dilution series was transferred to 96-well assay plates. Assay plates were inoculated with 90 μL of bacterial suspensions and incubated at 35-37° C. for 20 hrs. The assay plates were read using a microtiter plate reader (Molecular Devices) at 600 nm as well as by visual observation with a reading mirror. The lowest concentration of the compound that prevented visible growth was recorded as the MIC. Performance of the assay was monitored by testing aztreonam against laboratory quality control strains in accordance with guidelines of the CLSI.

Reference compounds: for comparison, the following known monobactam compounds are used herein:

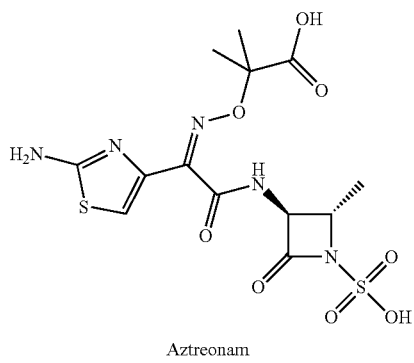

Reference compound 1

Aztreonam

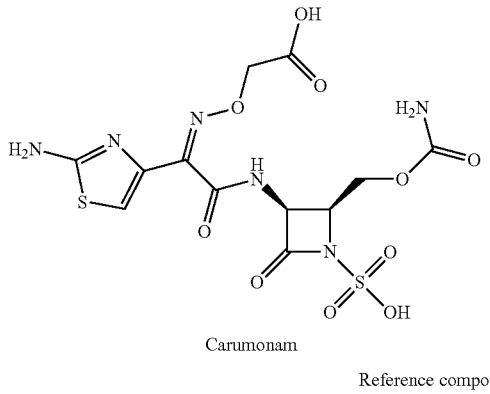

Reference compound 2

Carumonam

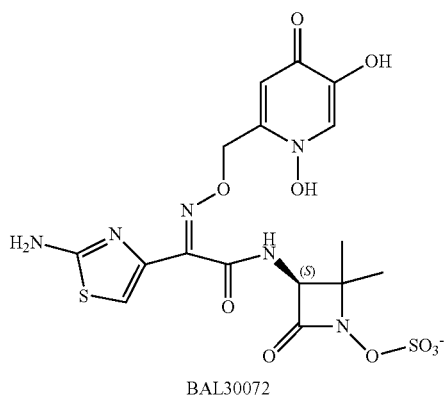

Reference compound 3

BAL30072

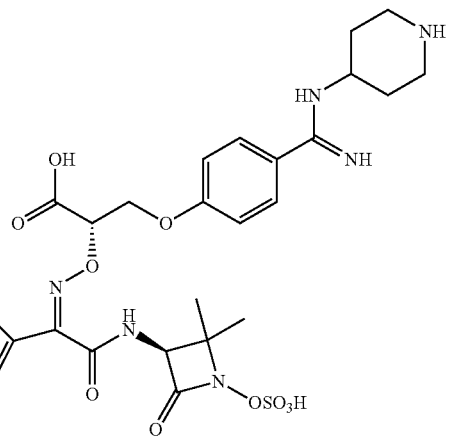

Reference compound 4

Aicuris WO2013110643

TABLE A

Minimum Inhibitory Concentrations (MIC) against isogenic strains of E. coli, carrying various resistance determinants.

| Example number | Strain 1 MIC (μg/mL) | Strain 2 MIC (μg/mL) | Strain 3 MIC (μg/mL) |
|---|---|---|---|
| Reference compound 1 | 0.125 | >32 | >32 |
| Reference compound 2 | 0.125 | 1 | >32 |
| Reference compound 3 | 0.25 | 0.5 | >32 |
| Reference compound 4 | ≤0.06 | 0.25 | 32 |
| Compound X | ≤0.06 | 0.125 | 0.5 |

Strain 1: E. coli NB27273-CDY0026 (parent)
Strain 2: E. coli NB27273-CDY0033 (KPC2)
Strain 3: E. coli NB27273-CDY0030 (SHV12)

The data in Table A show that Compound X has good antibacterial potency against E. coli, including strains that show strong resistance to several known monobactam and sulfactam antibiotics.

Additional activity data for Compound X is provided in the following table. Compound X was tested on E. coli strain 25922 and an E. coli containing KPC-2 (Strain 2 above, which is a known carbapenemase from Klebsiella pneumoniae), and exhibited these Inhibitory Concentrations (MIC), in mg/mL.

| Compound X | Salt | Ec 25922 | Ec KPC2 Iso |
|---|---|---|---|
| (structure) | none | 0.25 | 0.125 |

The invention claimed is:

1. An (L)-arginine salt of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid.

2. A sodium salt of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid.

3. A hydrated solid form of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid, wherein the hydrated solid form consists mainly of a trihydrate of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid.

4. A method to prepare the hydrated solid form according to claim 3, which comprises contacting 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic acid with an atmosphere having relative humidity between 25% and 50% at a temperature between 20° C. and 30° C.

5. A pharmaceutical composition comprising a compound according to any one of claims 1-3 and at least one pharmaceutically acceptable carrier or excipient.

6. A pharmaceutical composition comprising an (L)-arginine salt of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy) cyclopropanecarboxylic.

7. A pharmaceutical composition comprising a sodium salt of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid.

8. A pharmaceutical composition comprising a trihydrate of 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid.

9. A method of treatment for a Gram-negative infection, comprising administering to a subject in need thereof a therapeutically effective amount of a compound according to any one of claims 1-3, or a pharmaceutical composition according to any one of claims 6, 7, and 8.

* * * * *